United States Patent
Jones et al.

(10) Patent No.: US 11,167,007 B2
(45) Date of Patent: Nov. 9, 2021

(54) FOXM1 MODULATORS AND USES THEREOF

(71) Applicant: City of Hope, Duarte, CA (US)

(72) Inventors: Jeremy Jones, Sierra Madre, CA (US); Maya Otto-Duessel, Glendale, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 16/323,032

(22) PCT Filed: Aug. 1, 2017

(86) PCT No.: PCT/US2017/044834
§ 371 (c)(1),
(2) Date: Feb. 4, 2019

(87) PCT Pub. No.: WO2018/026776
PCT Pub. Date: Feb. 8, 2018

(65) Prior Publication Data
US 2019/0167756 A1   Jun. 6, 2019

Related U.S. Application Data

(60) Provisional application No. 62/370,925, filed on Aug. 4, 2016.

(51) Int. Cl.
| | |
|---|---|
| *A61K 38/12* | (2006.01) |
| *A61P 21/00* | (2006.01) |
| *A61K 38/17* | (2006.01) |
| *A61K 31/4709* | (2006.01) |
| *A61K 45/06* | (2006.01) |

(52) U.S. Cl.
CPC .......... *A61K 38/12* (2013.01); *A61K 31/4709* (2013.01); *A61K 38/1709* (2013.01); *A61K 45/06* (2013.01); *A61P 21/00* (2018.01)

(58) Field of Classification Search
CPC .... A61K 38/12; A61K 31/4709; A61K 45/06; A61K 38/1709; A61P 21/00
See application file for complete search history.

(56) References Cited

U.S. PATENT DOCUMENTS

| | | | |
|---|---|---|---|
| 2008/0057068 A1* | 3/2008 | Dalton | A61K 38/35 424/141.1 |
| 2008/0152618 A1* | 6/2008 | Gartel | A61P 35/00 424/85.1 |
| 2009/0156614 A1 | 6/2009 | Dalton et al. | |
| 2014/0011774 A1* | 7/2014 | Dalton et al. | |

OTHER PUBLICATIONS

Pandit et al., Prostate, 70(8): 825-833, Jun. 1 (Year: 2010).*
International Search Report dated Feb. 14, 2018, for PCT Application No. PCT/US2017/044834, filed Aug. 1, 2017, 7 pages.
Liu, Y. et al. (2014, e-published Feb. 27, 2014). "FOXM1 and androgen receptor co-regulate CDC6 gene transcription and DNA replication in prostate cancer cells," *Biochim Biophys Acta* 1839(4):297-305.
Written Opinion dated Feb. 14, 2018, for PCT Application No. PCT/US2017/044834, filed Aug. 1, 2017, 9 pages.

* cited by examiner

*Primary Examiner* — Kimberly Ballard
*Assistant Examiner* — Stacey N Macfarlane
(74) *Attorney, Agent, or Firm* — Mintz, Levin, Cohn, Ferris, Glovsky and Popeo, P.C.

(57) ABSTRACT

Disclosed herein, inter alia, are FOXM1 modulators and methods for modulating the activity of androgen receptors in neuronal cells to treat various diseases, such as spinal-bulbar muscular atrophy, amyotrophic lateral sclerosis, and Alzheimer's disease.

4 Claims, 6 Drawing Sheets

Specification includes a Sequence Listing.

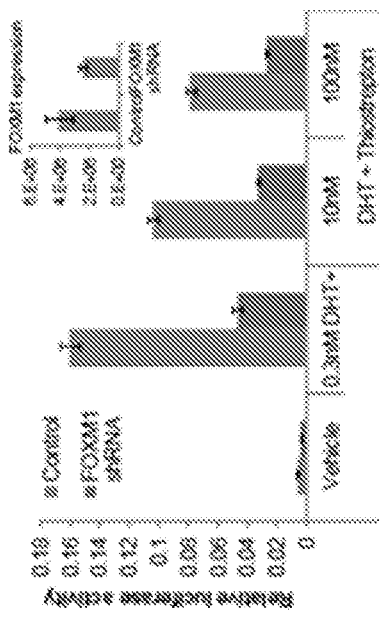
FIG. 3A
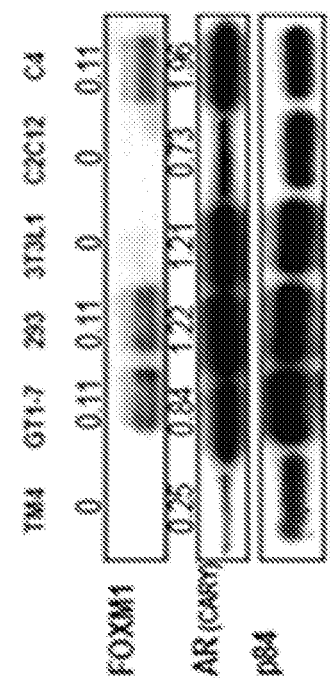
FIG. 3B
FIG. 3C
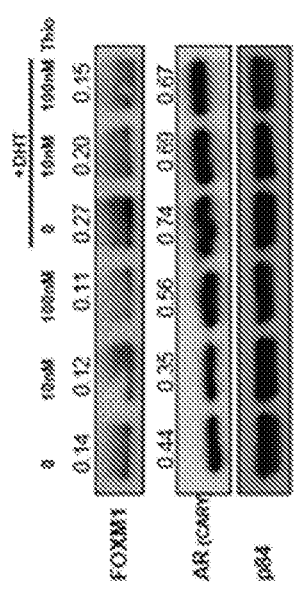
FIG. 3D
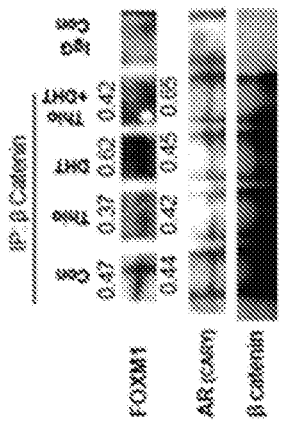
FIG. 3E
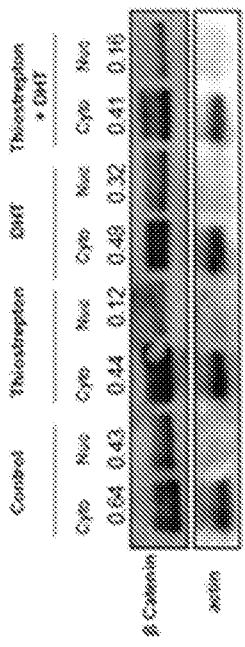

FOXM1 MODULATORS AND USES THEREOF

CROSS-REFERENCE TO RELATED APPLICATION

This application is a US national phase under 35 U.S.C. 371 of International Application No. PCT/US2017/044834 filed Aug. 1, 2017, which claims priority to U.S. Application No. 62/370,925 filed Aug. 4, 2016, which are incorporated by reference herein in their entirety.

BACKGROUND

Androgen receptor (AR) is a member of the nuclear hormone receptor family activated by androgens, such as dihydrotestosterone (DHT). AR is a prime therapeutic target for treating prostate cancer. Several compounds have been developed as chemotherapy for prostate cancer.

Androgen receptor competitive antagonists (antiandrogens) are drugs used to treat hormonal-based syndromes and prostate cancer. Current drugs for prostate cancer include flutamide, bicalutamide, nilutamide, enzalutamide and ARN-509. Each of these inhibitors binds to the hormone-binding pocket (HBP) of the androgen receptor. This is the same site that the natural physiological steroids testosterone (TES) and dihydrotestosterone (DHT) bind. The drugs work by competing with the natural hormones for binding to the pocket and, as a result, lessening activation of the receptor. Androgen receptor inhibitors with different mechanisms of action and/or different binding sites would be complementary to the current commercially available antagonists.

Spinal-bulbar muscular atrophy (SBMA) is a neuromuscular disorder of males with a prevalence of about $1/50,000$. The symptoms typically begin in the $4^{th}$ or $5^{th}$ decade of life, and include progressive weakness due to degeneration of motor neurons in the brain stem and spinal cord. Brooks et al, Trends Neurosci, 18(10):459-61 (1995). Currently, there is no means to prevent or treat the symptoms of SBMA. SBMA manifestations are dependent on androgen activation of a mutant AR with an expanded N-terminal polyglutamine tract. Fischbeck et al, Philos Trans R Soc Lond B Biol Sci, 354(1386):1075-8 (1999). Although the exact mechanism of toxicity is still under investigation, activation of AR in motor neurons causes them to die, leading to muscle atrophy. While studies in animal models demonstrate that inhibition of AR through androgen deprivation strategies (castration or suppression of testicular testosterone production) can ameliorate the disease manifestations associated with SBMA, similar studies in humans have not produced similar results. Katsuno et al, Neuron, 2002. 35(5):843-54 (2002); Katsuno et al, Nat Med, 9(6):768-73 (2003); Fischbeck et al, Ann Neurol, 65(2):119-20 (2009); Fernandez-Rhodes et al, Lancet Neurol, 10(2): p 140-7 (2011); Weydt et al. J Mol Neurosci, 2015.

One reason for the lack of efficacy in humans may be that systemic AR inhibition can also lead to muscle mass decrease by inhibiting anabolic AR activity in muscle cells. Storer et al, Asian J Androl, 14(2):204-21 (2012). In essence, systemic AR inhibition might improve motor neuron disease but prevent rescue of muscle symptoms. Therefore, the ability to inhibit AR selectively in the motor neurons could ameliorate the symptoms of SBMA. However, there is an ongoing debate about the contribution of mutant AR in motor neurons versus muscle cells in the pathogenesis of SBMA. Sobue et al, Brain, 1989. 112 (Pt 1): p. 209-32; Cortes et al, Neuron, 82(2):295-307 (2014); Lieberman et al, Cell Rep, 7(3):774-84 (2014); Rinaldi et al, J Mol Neurosci, 2015. Systemic treatment of BAC fxAR121 and AR113Q mice with antisense oligonucleotides (ASO) that silence mutant AR led to improvement of SBMA symptoms, suggesting a direct effect on mutant AR in muscle cells as ASO cannot cross the blood-brain barrier. Indeed, when administered directly into the CNS amelioration of the pathological phenotype was not achieved. Sobue et al, Brain, 112 (Pt 1):209-32 (1989). However, using a different transgenic mouse model of SBMA, AR97Q mice showed significant improvement after administration of ASO into the brain. Sahashi et al, Hum Mol Genet, 2015.

Thus, there is a need in the art for methods of treating androgen-receptor activity-associated diseases. Provided herein are solutions to these and other problems in the art.

BRIEF SUMMARY

The disclosure provides, inter alia, FOXM1 modulators, such as FOXM1 inhibitors, and methods of treating androgen-receptor activity-associated diseases, spinal-bulbar muscular atrophy, amyotrophic lateral sclerosis, and Alzheimer's disease in subjects in need of such treatment, where the methods include administering therapeutically effective amount of a FOXM1 modulator.

In aspects, the disclosure provides methods of treating spinal-bulbar muscular atrophy in a subject in need thereof by administering a therapeutically effective amount of a FOXM1 inhibitor to treat the spinal-bulbar muscular atrophy.

In aspects, the disclosure provides methods of reducing the level of androgen receptor activity in a motor neuron by contacting the motor neuron with an effective amount of a FOXM1 inhibitor to reduce the level of androgen receptor activity in the motor neuron.

In aspects, the disclosure provides methods of treating an androgen receptor activity-associated disease in a subject in need thereof by administering a therapeutically effective amount of a FOXM1 inhibitor to treat the androgen receptor activity-associated disease.

In aspects, the disclosure provides methods of treating prostate cancer, benign prostatic hyperplasia, hypersexuality, acne, amenorrhea, seborrhea, hirsutism, androgenic alopecia, hidradenitis suppurativa, spinal-bulbar muscular atrophy, Alzheimer's Disease, amyotrophic lateral sclerosis, or hyperandrogenism in a subject in need thereof by administering a therapeutically effective amount of a FOXM1 inhibitor.

In aspects, the disclosure provides methods of treating amyotrophic lateral sclerosis in a subject in need thereof by administering a therapeutically effective amount of a FOXM1 inhibitor to treat the amyotrophic lateral sclerosis.

In aspects, the disclosure provides methods of treating Alzheimer's disease in a subject in need thereof by administering a therapeutically effective amount of a FOXM1 inhibitor to treat the Alzheimer's disease.

In aspects, the FOXM1 inhibitors are antibiotics, such as thiazole antibiotics.

These and other aspects are described herein.

BRIEF DESCRIPTION OF THE DRAWINGS

FIG. 1A shows that AR conformation change can be monitored by the CFP-AR-YFP FRET reporter (top), and that screening for compounds that affect AR conformation change in GT1-7 cells was accomplished in 96 well plates.

FIG. 1B shows that hits were assessed for a dose response in the same assay, where the dose response to NSC285116 (siomycin A) is shown.

FIG. 2A shows that GT1-7 and C2C12 cells were transfected with androgen-responsive and control luciferase reporters and treated with the indicated drugs overnight. Both thiazole antibiotics siomycin and thiostrepton, as well as the selective FOXM1 inhibitor FDI-6, inhibited AR activity in GT1-7 but not C2C12 cells, with thiostrepton being the most potent of the drugs in this assay. FIG. 2B shows that rat L6 myoblasts and ReNcell CX and PC12 (ARQ112) neuronal cells were transfected with androgen-responsive and control luciferase reporters and treated with thiostrepton overnight. Thiostrepton inhibited AR luciferase activity in neuronal, but not muscle cells. FIG. 2C shows that 293 cells were transfected with androgen-responsive and control luciferase reporters as well as plasmids containing AR with 24 (normal state) or 65 (disease state) glutamines and treated with drugs mentioned above overnight. Both normal and disease state AR activity was reduced by thiostrepton treatment. Error bars represent the mean±SEM, *$P<0.05$.

FIGS. 3A-3E show that FOXM1 expression correlates with AR activity. FIG. 3A shows that expression of FOXM1 and AR was assessed by Western blot in indicated cell lines. FIG. 3B shows that GT1-7 cells were transfected with a lentiviral plasmid shRNA targeting FOXM1 as well as luciferase plasmids, treated with drugs listed, then assessed by luciferase assay. Decreased expression of FOXM1 (RT-qPCR in inset) reduced AR activity and diminished sensitivity to thiostrepton. Fold changes and p values are shown. FIG. 3C is a Western blot analysis that demonstrates that thiostrepton reduces FOXM1 levels in GT1-7 cells while DHT increases FOXM1 levels. FIG. 3D show that GT1-7 cells were treated with the indicated drugs overnight, and nuclear and cytoplasmic fractions were probed by Western blot for the indicated proteins. β-catenin levels in nuclear fraction of thiostrepton treated cells were lower compared to untreated ones. Quantification of β-catenin levels relative to cytoplasmic actin expression is shown. FIG. 3E shows that β-catenin was immunoprecipitated from GT1-7 cell lysates and Western blot was performed to detect AR and FOXM1. Quantification of AR and FOXM1 levels relative to β-catenin levels in IP is shown.

FIG. 4-B show that DHT promotes nuclear co-localization of AR and FOXM1.

FIG. 5A shows that rats (n=3) were administered 1, 10, or 100 mg/kg intraperitoneal injections thrice per week for four weeks. One hour following the final dose, blood and spinal fluid were collected and analyzed by mass spectrometry. Thiostrepton displayed the expected dose response in the serum, but much less was found in the cerebral spinal fluid. In FIGS. 5B-5F, rats (n=7) were treated with 100 mg/kg/day thiostrepton or vehicle for four weeks using intraperitoneally implanted osmotic pumps. Intact and castrate cohorts were included as controls. With reference to FIGS. B and C, immunohistochemistry revealed a reduction in the expression of FOXM1 in spinal cords compared to untreated (intact or castrate) animals. AR staining was also strong in the neurons. FIG. 5C shows that FOXM1 staining intensity was quantified by a veterinary pathologist (left) or by ImageJ (right) and found to be significantly reduced by thiostrepton treatment. FIG. 5D showed that IHC revealed weak to no FOXM1 staining in LA muscle tissue while AR staining was prevalent. FIG. 5E showed that, when tissues were harvested and weighed, castration significantly reduced the weight of the LA muscle ($p<0.01$) and seminal vesicles (SV) ($p<0.01$) compared to intact animals while thiostrepton treatment did not. With reference to FIGS. 5F-5H, RT-qPCR was used to quantify the levels of androgen-regulated transcripts in spinal cord (FIG. 5F) or LA muscle tissue (FIG. 5H or FOXM1-regulated transcripts in spinal cord (FIG. 5G). These figures show that thiostrepton was able to decrease the levels of androgen-regulated transcripts in spinal cords to a similar or greater extent than castration, demonstrating inhibition of AR activity, while in LA muscle, castration had a much stronger effect on AR activity than thiostrepton treatment. Two FOXM1 target gene transcripts were decreased with thiostrepton treatment, demonstrating an on target effect of the drug. Error bars represent the mean±SEM, $^aP<0.05$ ($P<0.08$ in FIG. 5G).

DETAILED DESCRIPTION

Figure 1A:
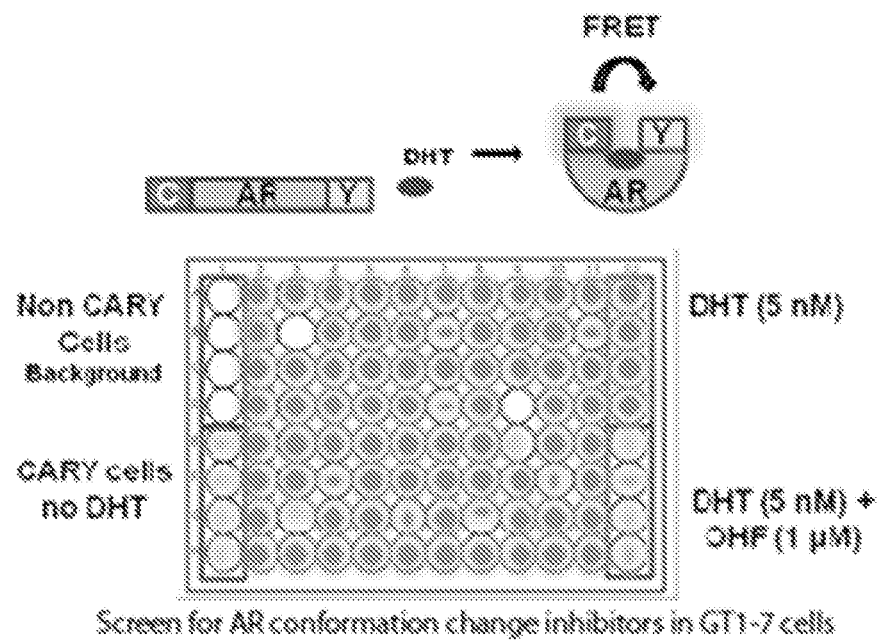
FIGS. 1A-1B show screening for neuron-selective AR inhibitors.

The abbreviations used herein have their conventional meaning within the chemical and biological arts. The chemical structures and formulae set forth herein are constructed according to the standard rules of chemical valency known in the chemical arts.

"Substituent group" or "substituent" means a group selected from the following moieties: (A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from: (i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from: (a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl. In embodiments, a "substituent group" or "substituent" is a "size-limited substituent" or "size-limited substituent group." In embodiments, a "substituent group" or "substituent" is a "lower substituent" or "lower substituent group."

"Size-limited substituent" or "size-limited substituent group" means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

"Lower substituent" or "lower substituent group" means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). In embodiments, "alkyl" is $C_{1-6}$ alkyl, or $C_{1-4}$ alky, or $C_{1-2}$ alkyl. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

"Alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

"Heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

"Heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

"Halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

"Acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

"Aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⤳" denotes the point of attachment of a chemical moiety to the remainder of a molecule or chemical formula.

"Oxo," as used herein, means an oxygen that is double bonded to a carbon atom.

"Alkylarylene" as an arylene moiety covalently bonded to an alkylene moiety (also referred to herein as an alkylene linker). In embodiments, the alkylarylene group has the formula:

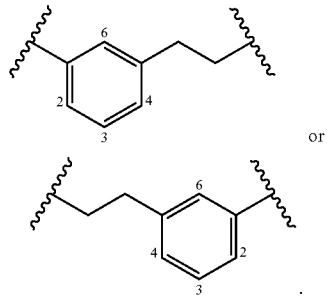

or

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, —$NHNH_2$, —$ONH_2$, —NHC(O)$NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR"R'")=NR"", —NR—C(NR"R")=NR'", —S(O)R', —S(O)₂R', —S(O)₂NR'R", —NRSO₂R', —NR'NR"R'", —ONR'R", —NR'C(O)NR"NR'"R"", —CN, —NO₂, —NR'SO₂R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO₂R', —CONR'R", —OC(O)NR'R", —NR"C(O)R', C(O)NR"R", —NR"C(O)₂R', —NR—C(NR'R"R'")=NR"", —NR—C(NR'R")=NR'", —S(O)R', —S(O)₂R', —S(O)₂NR'R", —NRSO₂R', —NR'NR"R'", —ONR'R", —NR'C(O)NR"NR'"R"", —CN, —NO₂, —R', —N₃, —CH(Ph)₂, fluoro(C₁-C₄)alkoxy, and fluoro(C₁-C₄)alkyl, —NR'SO₂R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR)$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH₂)$_r$—B—, wherein A and B are independently —CRR'—, —O—, —NR—, —S—, —S(O)—, —S(O)₂—, —S(O)₂NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —S—, —S(O)—, —S(O)₂—, or —S(O)₂NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

"Heteroatom" or "ring heteroatom" are meant to include oxygen (O), nitrogen (N), sulfur (S), phosphorus (P), and silicon (Si).

In embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

"Pharmaceutically acceptable salts" is meant to include salts of the active compounds that are prepared with relatively nontoxic acids or bases, depending on the particular substituents found on the compounds described herein. When compounds described herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain compounds contain both basic and acidic functionalities that allow the compounds to be converted into either base or acid addition salts. Other pharmaceutically acceptable carriers are known to those of skill in the art. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds described herein may exist as salts, such as with pharmaceutically acceptable acids. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds may be regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system. For example, physiologically hydrolyzable esters or amides are esters or amides, respectively, that are hydrolyzed to the corresponding hydroxyl and carboxylic acid portions of the ester, or the corresponding amine and carboxylic acid portions of the amide, by a chemical or enzymatic reaction (e.g., esterase or amidase or protease) following administration to a subject.

"Analog" and "analogue" are used interchangeably and are used in accordance with their plain ordinary meaning within chemistry and biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

"Derivative" is used in accordance with its plain ordinary meaning within chemistry and biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof; and the derivative is a compound that was derived from the reference compound through one or more chemical reaction(s) or the reference compound was derived from the derivative through one or more chemical reaction(s). Accordingly, a derivative is a compound that is similar or comparable in function and appearance but not in structure or origin to a reference compound. In embodiments of a derivative, an original substituent (e.g., substituent group) of a reference compound is replaced with an alternative substituent (e.g., substituent group), wherein the alternative substituent (e.g., substituent group) is different from the original substituent (e.g., substituent group). In embodiments of a derivative, a plurality of original substituents (e.g., substituent groups) of a reference compound are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of a reference compound is replaced with a substituent (e.g., substituent group). In embodiments of a derivative, a plurality of hydrogen atoms of a reference compound are replaced with a plurality of substituents (e.g., substituent groups), wherein the substituents (e.g., substituent groups) are each optionally different. A "derivative" may also be referred to herein as a "substituted" compound.

"About" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

Certain compounds described herein can exist in unsolvated forms as well as solvated forms, including hydrated forms. In general, the solvated forms are equivalent to unsolvated forms and are encompassed within the scope of the disclosure. Certain compounds described herein may exist in multiple crystalline or amorphous forms. In general, all physical forms are equivalent for the uses contemplated and are intended to be within the scope of the disclosure.

"Salt" refers to acid or base salts of the compounds described herein. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds described herein possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the disclosure. The disclosure includes compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

"Isomers" refers to compounds having the same number and kind of atoms, and hence the same molecular weight, but differing in respect to the structural arrangement or configuration of the atoms.

"Tautomer" refers to one of two or more structural isomers which exist in equilibrium and which are readily converted from one isomeric form to another. It will be apparent to one skilled in the art that certain compounds described herein may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the disclosure. The compounds described herein may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds described herein, whether radioactive or not, are encompassed within the scope of the disclosure.

"A" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

"Spinal and bulbar muscular atrophy," "Spinal-bulbar muscular atrophy," "SBMA," "spinobulbar muscular atrophy," "bulbo-spinal atrophy," "X-linked bulbospinal neuropathy," "XBSN," "X-linked spinal muscular atrophy type 1," "SMAX1," "Kennedy's disease," and "KD" are used interchangeably according to their common usage in the art and all refer to a neurodegenerative disorder resulting in muscle cramps and progressive weakness due to degeneration of motor neurons in the brain stem and/or spinal cord. The degeneration of the motor neurons may result from CAG expansion of the androgen receptor gene leading to polyQ tract expansion in the androgen receptor protein.

"Motor neuron" is a cell located in the central nervous system (e.g., spinal cord or brain stem) that comprises an axon projecting outside of the central nervous system (e.g., spinal cord or brain stem) that controls (e.g., through electrical impulses) a muscle, gland, or other effector tissue. In embodiments, the motor neuron is a motor neuron in the spinal cord. In embodiments, the motor neuron is a motor neuron in the brain stem.

"Treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination.

"Effective amount" or "therapeutically effective amount" is an amount sufficient to accomplish a stated purpose (e.g. achieve the effect for which it is administered, treat a disease, prevent a disease, reduce enzyme activity, increase enzyme activity, reduce protein function, prevent or reduce one or more symptoms of a disease). In embodiments, a therapeutically effective amount is an amount sufficient to treat SBMA, amyotrophic lateral sclerosis, or Alzheimer's disease, as described herein. An example of an effective amount is an amount sufficient to contribute to the treatment, prevention, or reduction of a symptom or symptoms of a disease. "Reducing" a symptom or symptoms means decreasing the severity or frequency of the symptom(s), or elimination of the symptom(s). The exact amount of an effective dose will depend on the purpose of the treatment and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

"Associated" or "associated with" in the context of a substance or substance activity or function associated with a disease (e.g., spinal-bulbar muscular atrophy, Alzheimer's Disease, amyotrophic lateral sclerosis) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with androgen receptor activity may be treated with an agent (e.g., FOXM1 inhibitor as described herein) effective for decreasing the level of androgen receptor activity.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, a control is a subject without a disease (e.g., spinal-bulbar muscular atrophy, Alzheimer's Disease, amyotrophic lateral sclerosis). In embodiments, a control is a subject without a mutation in a protein (e.g., androgen receptor). In embodiments, a control is a subject (e.g., a statistical group average) not receiving a treatment (e.g., a FOXM1 inhibitor described herein).

"Contacting" is used in accordance with its plain ordinary meaning and refers to the process of allowing at least two distinct species (e.g. chemical compounds including FOXM1 inhibitors and neurons) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein, enzyme, motor neuron, or cell.

"Inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

"Activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

"Modulator" refers to a compound or composition that increases or decreases the level of a target molecule or the function of a target molecule. In embodiments, a modulator is a FOXM1 inhibitor. In embodiments, a modulator is an androgen receptor activity inhibitor. A FOXM1 modulator is a composition that increases or decreases the level of FOXM1 (e.g., protein, mRNA) or the level of activity of FOXM1 (e.g., transcriptional activation, transcriptional activity, binding to a second protein, induction of androgen receptor expression, or induction of androgen receptor activity). In embodiments, a FOXM1 modulator decreases the level of FOXM1 (e.g., protein, mRNA) or the level of activity of FOXM1 (e.g., transcriptional activation, transcriptional activity, binding to a second protein, induction of androgen receptor expression, or induction of androgen receptor activity) (i.e., FOXM1 inhibitor). In embodiments, a FOXM1 modulator decreases the level of FOXM1 protein. In embodiments, a FOXM1 modulator decreases the level of FOXM1 mRNA. In embodiments, a FOXM1 modulator decreases the level of activity of FOXM1. In embodiments, a FOXM1 modulator increases the level of FOXM1 (e.g., protein, mRNA) or the level of activity of FOXM1 (e.g., transcriptional activation, transcriptional activity, binding to a second protein, induction of androgen receptor expression, or induction of androgen receptor activity) (i.e., FOXM1 activator). In embodiments, the FOXM1 inhibitor selectively inhibits androgen receptor activity in a neuronal cell. In embodiments, the FOXM1 inhibitor selectively inhibits androgen receptor activity in a neuronal cell when compared to a muscle cell (e.g., the FOXM1 inhibitor inhibits androgen receptor activity in a neuronal cell but does not inhibit androgen receptor activity in a muscle cell).

"Patient" or "subject" refers to a living organism suffering from or prone to a disease or condition (e.g., spinal-bulbar muscular atrophy, amyotrophic lateral sclerosis, Alzheimer's disease) that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is a disease having the symptom of an aberrant level of androgen receptor activity. In some embodiments, the disease is spinal-bulbar muscular atrophy. In some embodiments, the disease is Alzheimer's Disease. In some embodiments, the disease is amyotrophic lateral sclerosis.

"Signaling pathway" as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propagated to other signaling pathway components.

"Aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. Nucleic acids containing one or more carbocyclic sugars are also included within one definition of nucleic acids.

A particular nucleic acid sequence also encompasses "splice variants." Similarly, a particular protein encoded by a nucleic acid encompasses any protein encoded by a splice variant of that nucleic acid. "Splice variants" are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative.

"Identical" or "identity" in the context of two or more nucleic acids or polypeptide sequences refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods. For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

"Comparison window" includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

"Selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

"Stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. Substitution of one amino acid residue for another from a different class or group is referred to herein as a "non-conservative" substitution. In contrast, non-conservative amino acid substitutions tend to modify conformation and function of a protein. Examples of amino acid classifications include: (i) small/aliphatic residues: Gly, Ala, Val, Leu, Ile; (ii) cyclic imino acid: Pro; (iii) hydroxyl-containing residues: Ser, Thr; (iv) acidic residues: Asp, Glu; (v) amide residue: Asn, Gln; (vi) basic residues: Lys, Arg; (vii) imidazole residue: His; (viii) aromatic residues: Phe, Tyr, Trp; and (ix) sulfur-containing residues: Met, Cys.

In embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., Biochemistry at pp. 13-15, 2nd ed. Lubert Stryer ed. (Stanford University); Henikoff et al., Proc. Nat'l Acad. Sci. USA, 89:10915-10919 (1992); Lei et al., J. Biol. Chem. (1995) 270(20):11882-11886).

Following expression, the proteins can be isolated. The term "purified" or "isolated" as applied to any of the proteins described herein refers to a polypeptide that has been separated or purified from components (e.g., proteins or other naturally-occurring biological or organic molecules) which naturally accompany it, e.g., other proteins, lipids, and nucleic acid in a cell expressing the proteins. Typically, a polypeptide is purified when it constitutes at least 60 (e.g., at least 65, 70, 75, 80, 85, 90, 92, 95, 97, or 99) %, by weight, of the total protein in a sample.

An amino acid residue in a protein "corresponds" to a given residue when it occupies the same essential structural position within the protein as the given residue. Instead of a primary sequence alignment, a three dimensional structural alignment can also be used, e.g., where the structure of the selected protein is aligned for maximum correspondence with the human androgen receptor protein and the overall structures compared.

"Pharmaceutically acceptable excipient" and "pharmaceutically acceptable carrier" refer to a substance that aids the administration of an active agent to and absorption by a subject and can be included in the compositions of the disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds described herein. One of skill in the art will recognize that other pharmaceutical excipients can be used.

"Preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

"Administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies. The compounds described herein can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions described herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions described herein may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions described herein can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). In another embodiment, the formulations of the compositions described herein can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions described herein into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions described herein can also be delivered as nanoparticles.

Pharmaceutical compositions described herein include compositions wherein the active ingredient (e.g. compounds described herein, including embodiments or examples) is contained in a therapeutically effective amount. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms, e.g. symptoms of spinal-bulbar muscular atrophy, Alzheimer's Disease, amyotrophic lateral sclerosis, or aberrant androgen receptor activity. Determination of a therapeutically effective amount of the compounds described herein is within the capabilities of a skilled artisan, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of spinal-bulbar muscular atrophy, Alzheimer's Disease, amyotrophic lateral sclerosis), kind of concurrent treatment, complications from the disease being treated or other health-related problems. Other therapeutic regimens or agents can be used in conjunction with the methods and compounds described herein. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments such as an androgen receptor inhibitor or surgery.

"Androgen receptor" or "AR" or "NR3C4" refers to a nuclear receptor activated by binding of the androgenic hormone testosterone or dihydrotestosterone. "Androgen receptor" may refer to the nucleotide sequence or protein sequence of human androgen receptor (e.g., Entrez 367, Uniprot P10275, RefSeq NM 000044, or RefSeq NP_000035). "Androgen receptor" includes both the wild-type form of the nucleotide sequences or proteins as well as any mutants thereof. In embodiments, "androgen receptor" is wild-type androgen receptor. In embodiments, "androgen receptor" is one or more mutant forms. In embodiments, "androgen receptor" XYZ refers to a nucleotide sequence or protein of a mutant androgen receptor wherein the Y numbered amino acid of androgen receptor that normally has an X amino acid in the wildtype, instead has a Z amino acid in the mutant. In embodiments, an androgen receptor is the human androgen receptor. In embodiments, the androgen receptor has the nucleotide sequence corresponding to reference number GI:349501065. In embodiments, the androgen receptor has the nucleotide sequence corresponding to RefSeq NM_000044.3. In embodiments, the androgen receptor has the protein sequence corresponding to reference number GI:21322252. In embodiments, the androgen receptor has the protein sequence corresponding to RefSeq NP_000035.2. In embodiments, the androgen receptor has the following amino acid sequence:

```
                                             (SEQ ID NO: 1)
MEVQLGLGRVYPRPPSKTYRGAFQNLFQSVREVIQNPGPRHPEAASAAPP

GASLLLLQQQQQQQQQQQQQQQQQQQQQQETSPRQQQQQQGEDGSPQAHRR

GPTGYLVLDEEQQPSQPQSALECHPERGCVPEPGAAVAASKGLPQQLPAP

PDEDDSAAPSTLSLLGPTFPGLSSCSADLKDILSEASTMQLLQQQQQEAV

SEGSSSGRAREASGAPTSSKDNYLGGTSTISDNAKELCKAVSVSMGLGVE

ALEHLSPGEQLRGDCMYAPLLGVPPAVRPTPCAPLAECKGSLLDDSAGKS

TEDTAEYSPFKGGYTKGLEGESLGCSGSAAAGSSGTLELPSTLSLYKSGA

LDEAAAYQSRDYYNFPLALAGPPPPPPPPHPHARIKLENPLDYGSAWAAA

AAQCRYGDLASLHGAGAAGPGSGSPSAAASSSWHTLFTAEEGQLYGPCGG

GGGGGGGGGGGGGGGGGGGGGEAGAVAPYGYTRPPQGLAGQESDFTAPD

VWYPGGMVSRVPYPSPTCVKSEMGPWMDSYSGPYGDMRLETARDHVLPID

YYFPPPQKTCLICGDEASGCHYGALTCGSCKVFFKRAAEGKQKYLCASRND

CIIDKFRRKNCPSCRLRKCYEAGMTLGARKLKKLGNLKLQEEGEASSTTS

PTEETTQKLTVSHIEGYECQPIFLNVLEAIEPGVVCAGHDNNQPDSFAAL

LSSLNELGERQLVHVVKWAKALPGFRNLHVDDQMAVIQYSWMGLMVFAMG

WRSFTNVNSRMLYFAPDLVFNEYRMHKSRMYSQCVRMRHLSQEFGWLQIT

PQEFLCMKALLLFSIIPVDGLKNQKFFDELRMNYIKELDRIIACKRKNPT

SCSRRFYQLTKLLDSVQPIARELHQFTFDLLIKSHMVSVDFPEMMAEIIS

VQVPKILSGKVKPIYFHTQ.
```

In embodiments, the androgen receptor is a mutant androgen receptor. In embodiments, the mutant androgen receptor is associated with a disease that is not associated with wildtype androgen receptor (e.g., spinal-bulbar muscular atrophy, Alzheimer's Disease, amyotrophic lateral sclerosis). In embodiments, the androgen receptor includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to SEQ ID NO:1. In embodiments, the mutant androgen receptor is a splice variant. In embodiments, the mutant androgen receptor is lacking a portion of the ligand binding domain. In embodiments, the mutant androgen receptor is active in the absence of bound ligand. In embodiments, the mutant androgen receptor is lacking the ligand binding domain. In embodiments, the mutant androgen receptor includes a polyQ expansion (e.g., compared to an androgen receptor sequence above).

"Forkhead Box Protein M1" or "FOXM1" refers to a transcription factor involved in cell cycle progression with peak endogenous expression at S and G2/M phases. "FOXM1" may refer to the nucleotide sequence or protein sequence of human FOXM1 (e.g., Entrez 2305, Uniprot Q08050, RefSeq NM_202002, or RefSeq NP_973731). "FOXM1" includes both the wild-type form of the nucleotide sequences or proteins as well as any mutants thereof. In embodiments, "FOXM1" is wild-type FOXM1. In embodiments, "FOXM1" is one or more mutant forms. "FOXM1 XYZ" refers to a nucleotide sequence or protein of a mutant FOXM1 wherein the Y numbered amino acid of FOXM1 that normally has an X amino acid in the wildtype, instead has a Z amino acid in the mutant. In embodiments, FOXM1 is the human FOXM1. In embodiments, FOXM1 has the nucleotide sequence corresponding to reference number GI:340545539. In embodiments, FOXM1 has the nucleotide sequence corresponding to RefSeq NM_202002.2. In embodiments, FOXM1 has the protein sequence corresponding to reference number GI:42544167. In embodiments, FOXM1 has the protein sequence corresponding to RefSeq NP_973731.1. In embodiments, FOXM1 has the following amino acid sequence:

(SEQ ID NO: 2)
MKTSPRRPLILKRRRLPLPVQNAPSETSEEEPKRSPAQQESNQAEASKEV

AESNSCKFPAGIKIINHPTMPNTQVVAIPNNANIHSIITALTAKGKESGS

SGPNKFILISCGGAPTQPPGLRPQTQTSYDAKRTEVTLETLGPKPAARDV

NLPRPPGALCEQKRETCADGEAAGCTINNSLSNIQWLRKMSSDGLGSRSI

KQEMEEKENCHLEQRQVKVEEPSRPSASWQNSVSERPPYSYMAMIQFAIN

STERKRMILKDIYTWIEDHFPYFKHIAKPGWKNSIRHNLSLHDMFVRETS

ANGKVSFWTIHPSANRYLTLDQVFKPLDPGSPQLPEHLESQQKRPNPELR

RNMTIKTELPLGARRKMKPLLPRVSSYLVPIQFPVNQSLVLQPSVKVPLP

LAASLMSSELARHSKRVRIAPKVFGEQVVFGYMSKFFSGDLRDFGTPITS

LFNFIFLCLSVLLAEEGIAPLSSAGPGKEEKLLFGEGFSPLLPVQTIKEE

EIQPGEEMPHLARPIKVESPPLEEWPSPAPSFKEESSHSWEDSSQSPTPR

PKKSYSGLRSPIRCVSEMLVIQHRERRERSRSRRKQHLLPPCVDEPELLF

SEGPSTSRWAAELPFPADSSDPASQLSYSQEVGGPFKTPIKETLPISSTP

SKSVLPRITESWRLTPPAKVGGLDFSPVQTSQGASDPLPDPLGLMDLSTT

PLQSAPPLESPQRLLSSEPLDLISVPFGNSSPSDIDVPKPGSPEPQVSGL

AANRSLTEGLVLDTMNDSLSKILLDISFPGLDEDPLGPDNINWSQFIPEL

Q.

In embodiments, FOXM1 is a mutant FOXM1. In embodiments, the mutant FOXM1 is associated with a disease that is not associated with wildtype FOXM1 (e.g., spinal-bulbar muscular atrophy, Alzheimer's Disease, amyotrophic lateral sclerosis). In embodiments, the FOXM1 includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to SEQ ID NO:2. In embodiments, the mutant FOXM1 is a splice variant.

"p14ARF" refers to a tumor suppressor which is expressed from an alternative reading frame of CDKN2A in humans. "p14ARF" includes both the wild-type form of the nucleotide sequence or protein as well as any mutants thereof. In embodiments, "p14ARF" is wild-type p14ARF. In embodiments, "p14ARF" is one or more mutant forms. "p14ARF XYZ" refers to a nucleotide sequence or protein of a mutant p14ARF wherein the Y numbered amino acid of p14ARF that normally has an X amino acid in the wildtype, instead has a Z amino acid in the mutant. In embodiments, the p14ARF has the following amino acid sequence:

(SEQ ID NO: 3)
MVRRFLVTLRIRRACGPPRVRVFVVHIPRLTGEWAAPGAPAAVALVLMLL

RSQRLGQQPLPRRPGHDDGQRPSGGAAAAPRRGAQLRRPRHSHPTRARRC

PGGLPGHAGGAAPGRGAAGRARCLGPSARGPG.

"p19ARF" refers to a tumor suppressor which is expressed from an alternative reading frame of CDKN2A in mice. "p19ARF" includes both the wild-type form of the nucleotide sequence or protein as well as any mutants thereof. In embodiments, "p19ARF" is wild-type p19ARF. In embodiments, "p19ARF" is one or more mutant forms. "p19ARF XYZ" refers to a nucleotide sequence or protein of a mutant p19ARF wherein the Y numbered amino acid of p19ARF that normally has an X amino acid in the wildtype, instead has a Z amino acid in the mutant. In embodiments, the p19ARF has the following amino acid sequence:

(SEQ ID NO: 4)
MGRRFLVTVRIQRAGRPLQERVFLVKFVRSRRPRTASCALAFVNMLLRLE

RTLRRGPHRNPGPGDDDGQRSRSSSSAQLRCRFELRGPHYLLPPGARRSA

GRLPGHAGGAARVRGSAGCARCLGSPAARLGPRAGTSRHRAIFAFRWVLF

VFRWVVFVYRWERRPDRRA.

"Thiazole antibiotic" refers to a compound that functions as an antibiotic and that includes one or more thiazole moieties. Exemplary thiazole antibiotics include 68-1147, A10255, A-8506, amythiamicin, berninamycin, bryamycin, cyclothiazomycin, GE2270, GE37468, geninthiocin, glycothiohexide, JBIR-83-4, methylsulfonycin, micrococcin, MJ347-81F4, multhiomycin, neoberninamycin, nocardithiocin, nocathiacin, nosiheptide, promoinducin, promothiocin, QN3323, radamycin, S-54832, Sch 18640, Sch 40832, siomycin, sulfomycin, thiactin, thioactin, thiocillin, thiomuracins, thiopeptin, thiostrepton, thiotipin, thioxamycin, TP-1161, or YM-266183-4, or a pharmaceutically acceptable salt, an analog, a derivative, or a prodrug of any one of the foregoing. The function of the compound can be the primary function, or can be a secondary or tertiary function of the compound.

FOXM1 Modulators

The disclosure provides a FOXM1 modulator or a pharmaceutically acceptable salt thereof. In embodiments, the FOXM1 modulator is a FOXM1 inhibitor. In embodiments, the FOXM1 modulator is a FOXM1 antagonist.

In embodiments, the FOXM1 modulator is a small molecule (e.g., molecular weight less than about 2000 Da, less than about 1000 Da, or less than about 500 Da). In embodiments, the FOXM1 modulator is a small molecule (e.g., less than about 2000 g/mol, less than about 1000 g/mol, less than about 500 g/mol, about 1000 to 2000 g/mol, about 1250 to 1750 g/mol, or about 1500 to 1700 g/mol).

In embodiments, the FOXM1 modulator is a thiazole antibiotic. In embodiments, the FOXM1 modulator is a thiazole containing small molecule (e.g., less than about 2000 g/mol, less than about 1000 g/mol, less than about 500 g/mol, about 1000 to 2000 g/mol, about 1250 to 1750 g/mol, or about 1500 to 1700 g/mol). In embodiments, the FOXM1 modulator is a thiazole containing antibiotic (e.g., less than about 2000 g/mol, less than about 1000 g/mol, less than about 500 g/mol, about 1000 to 2000 g/mol, about 1250 to 1750 g/mol, or about 1500 to 1700 g/mol). In embodiments, the FOXM1 modulator is a thiazole containing cyclic antibiotic (e.g., less than about 2000 g/mol, less than about 1000 g/mol, less than about 500 g/mol, about 1000 to 2000 g/mol, about 1250 to 1750 g/mol, or about 1500 to 1700 g/mol). In embodiments, the FOXM1 modulator is a thiazole containing cyclic oligopeptide (e.g., less than about 2000 g/mol, less than about 1000 g/mol, less than about 500 g/mol, about 1000 to 2000 g/mol, about 1250 to 1750 g/mol, or about 1500 to 1700 g/mol). In embodiments, the FOXM1 modulator is a thiazole containing cyclic oligopeptide antibiotic (e.g., less than about 2000 g/mol, less than about 1000 g/mol, less than about 500 g/mol, about 1000 to 2000 g/mol, about 1250 to 1750 g/mol, or about 1500 to 1700 g/mol). In embodiments, the FOXM1 modulator is a thiazole containing ribosomally synthesized and post-translationally modified peptide (RiPP) (e.g., less than about 2000 g/mol, less than about 1000 g/mol, less than about 500 g/mol, about 1000 to 2000 g/mol, about 1250 to 1750 g/mol, or about 1500 to 1700 g/mol). In embodiments, the FOXM1 modulator is a thiazole containing thiopeptide ribosomally synthesized and post-translationally modified peptide (RiPP) (e.g., less than about 2000 g/mol, less than about 1000 g/mol, less than about 500 g/mol, about 1000 to 2000 g/mol, about 1250 to 1750 g/mol, or about 1500 to 1700 g/mol). In embodiments, the FOXM1 modulator includes a thiazole. In embodiments, the FOXM1 modulator includes a plurality of thiazoles. In embodiments, the FOXM1 modulator includes a piperidine. In embodiments, the FOXM1 modulator includes a dehydropiperidine. In embodiments, the FOXM1 modulator includes a pyridine. In embodiments, the FOXM1 modulator includes a quinaldic acid. In embodiments, the FOXM1 modulator includes an indolic acid. In embodiments, the FOXM1 modulator includes an azoline. In embodiments, the FOXM1 modulator is about 100, 200, 300, 400, 500, 600, 700, 800, 900, 1000, 1100, 1200, 1300, 1400, 1500, 1600, 1700, 1800, 1900, or 2000 g/mol. In embodiments, the FOXM1 modulator is less than 100, 200, 300, 400, 500, 600, 700, 800, 900, 1000, 1100, 1200, 1300, 1400, 1500, 1600, 1700, 1800, 1900, or 2000 g/mol. In embodiments, the FOXM1 modulator is about 100 to 200, 200 to 300, 300 to 400, 400 to 500, 500 to 600, 600 to 700, 700 to 800, 800 to 900, 900 to 1000, 1000 to 1100, 1100 to 1200, 1200 to 1300, 1300 to 1400, 1400 to 1500, 1500 to 1600, 1600 to 1700, 1700 to 1800, 1800 to 1900, or 1900 to 2000 g/mol. In embodiments, the FOXM1 modulator is 100 to 200, 200 to 300, 300 to 400, 400 to 500, 500 to 600, 600 to 700, 700 to 800, 800 to 900, 900 to 1000, 1000 to 1100, 1100 to 1200, 1200 to 1300, 1300 to 1400, 1400 to 1500, 1500 to 1600, 1600 to 1700, 1700 to 1800, 1800 to 1900, or 1900 to 2000 g/mol.

In embodiments, the FOXM1 modulator is a polypeptide (e.g., oligomer of about 5 to 50 amino acids, about 10 to 40 amino acids, about 15 to 30 amino acids, about 15 to 25 amino acids, about 15 to 20 amino acids, or about 19 amino acids).

In embodiments, the FOXM1 modulator is a polypeptide having about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. In embodiments, the FOXM1 modulator is a polypeptide having 5 to 50 amino acids (e.g., having 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids). In embodiments, the FOXM1 modulator is a polypeptide having about 5 to 10, 11 to 15, 16 to 20, 21 to 25, 26 to 30, 31 to 35, 36 to 40, 41 to 45, or 46 to 50 amino acids. In embodiments, the FOXM1 modulator is a polypeptide having 5 to 10, 11 to 15, 16 to 20, 21 to 25, 26 to 30, 31 to 35, 36 to 40, 41 to 45, or 46 to 50 amino acids.

In embodiments, the FOXM1 modulator is a polypeptide comprising the amino acid sequence KFVRSRRPRTASCALAFVN (SEQ ID NO:5), KFVRSRRPRTASCALAFV (SEQ ID NO:6), KFVRSRRPRTASCALAF (SEQ ID NO:7), KFVRSRRPRTASCALA (SEQ ID NO:8), KFVRSRRPRTASCAL (SEQ ID NO:9), KFVRSRRPRTASCA (SEQ ID NO:10), KFVRSRRPRTASC (SEQ ID NO:11), KFVRSRRPRTAS (SEQ ID NO:12), KFVRSRRPRTA (SEQ ID NO:13), KFVRSRRPRT (SEQ ID NO:14), KFVRSRRPR (SEQ ID NO:15), KFVRSRRP (SEQ ID NO:16), KFVRSRR (SEQ ID NO:17), KFVRSR (SEQ ID NO:18), KFVRS (SEQ ID NO:19), FVRSRRPRTASCALAFVN (SEQ ID NO:20), VRSRRPRTASCALAFVN (SEQ ID NO:21), RSRRPRTASCALAFVN (SEQ ID NO:22), SRRPRTASCALAFVN (SEQ ID NO:23), RRPRTASCALAFVN (SEQ ID NO:24), RPRTASCALAFVN (SEQ ID NO:25), PRTASCALAFVN (SEQ ID NO:26), RTASCALAFVN (SEQ ID NO:27), TASCALAFVN (SEQ ID NO:28), ASCALAFVN (SEQ ID NO:29), SCALAFVN (SEQ ID NO:30), CALAFVN (SEQ ID NO:31), ALAFVN (SEQ ID NO:32), LAFVN (SEQ ID NO:33), FVRSRRPRTASCALAFV (SEQ ID NO:34), VRSRRPRTASCALAF (SEQ ID NO:35), RSRRPRTASCALA (SEQ ID NO:36), SRRPRTASCAL (SEQ ID NO:37), RRPRTASCA (SEQ ID NO:38), RPRTASC (SEQ ID NO:39), or KPRTAS (SEQ ID NO:40).

In embodiments, the FOXM1 inhibitor is a peptide comprising a sequence that is at least 50% identical, or at least 55% identical, or at least 60% identical, or at least 65% identical, or least 70% identical, or least 75% identical, or at least 80% identical, or at least 85% identical, or at least 90% identical, or at least 95% identical to SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18; SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27; SEQ ID NO:28, SEQ ID NO:29, SEQ ID NO:30, SEQ ID NO: 31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, or SEQ ID NO:40.

In embodiments, the FOXM1 inhibitor is a peptide comprising a sequence that is at least 50% identical, or at least 55% identical, or at least 60% identical, or at least 65% identical, or least 70% identical, or least 75% identical, or at least 80% identical, or at least 85% identical, or at least 90% identical, or at least 95% identical to SEQ ID NO:5. In embodiments, the FOXM1 modulator is a polypeptide comprising the amino acid sequence of SEQ ID NO:5.

In embodiments, the FOXM1 modulator is a polypeptide including a cell-penetrating peptide sequence (e.g., poly arginine sequence, 6 arginines, 7 arginines, 8 arginines, 9 arginines, 10 arginines, 11 arginines, 12 arginines, 13 arginines, 14 arginines, or 15 arginines). In embodiments, the FOXM1 modulator is a polypeptide including a cell-penetrating peptide sequence (e.g., poly arginine sequence, 6 arginines, 7 arginines, 8 arginines, 9 arginines, 10 arginines, 11 arginines, 12 arginines, 13 arginines, 14 arginines, or 15 arginines) at the N terminus. In embodiments, the FOXM1 modulator is a polypeptide including a cell-penetrating peptide sequence (e.g., poly arginine sequence, 6 arginines, 7 arginines, 8 arginines, 9 arginines, 10 arginines, 11 arginines, 12 arginines, 13 arginines, 14 arginines, or 15 arginines) at the C terminus. In embodiments, the FOXM1 modulator is a polypeptide including a fragment of the p14ARF protein of SEQ ID NO:3, e.g., where the fragment is 5 to 50 continuous amino acids of the protein (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 continuous amino acids of the protein). In embodiments, the FOXM1 modulator is a polypeptide including a fragment of the p19ARF protein of SEQ ID NO:4, wherein the fragment is 5 to 50 continuous amino acids of the protein (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 continuous amino acids of the protein). In embodiments, the FOXM1 modulator is described in Gusarova et al, The Journal of Clinical Investigation, 17(1):99-111 (2007), which is incorporated herein by reference in its entirety for all purposes.

In embodiments, the FOXM1 modulator is a peptide having a sequence that is at least 50% identical, or at least 55% identical, or at least 60% identical, or at least 65% identical, or at least 70% identical, or at least 75% identical, or at least 80% identical, or at least 85% identical, or at least 90% identical, or at least 95% identical to SEQ ID NO:3. In embodiments, the FOXM1 modulator is SEQ ID NO:3. In embodiments, the FOXM1 modulator is a peptide having a sequence that is at least 50% identical, or at least 55% identical, or at least 60% identical, or at least 65% identical, or at least 70% identical, or at least 75% identical, or at least 80% identical, or at least 85% identical, or at least 90% identical, or at least 95% identical to SEQ ID NO:4. In embodiments, the FOXM1 modulator is SEQ ID NO:4.

In embodiments, the FOXM1 modulator is FDI-2:

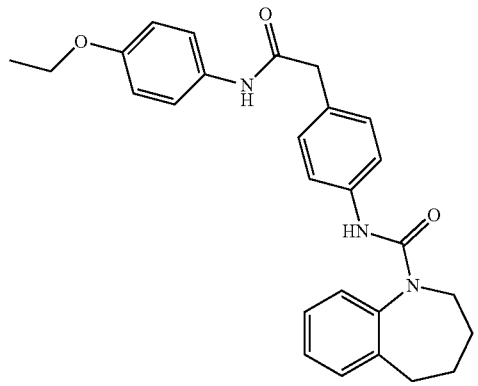 [SMILES: CCOc1ccc(NC(=O)Cc2ccc(NC(=O)N3CCCCc4ccccc43)cc2)cc1]

(FDI-2, NCGC00129183) or a derivative, an analog, or a prodrug thereof, or a pharmaceutically acceptable salt of any of the foregoing. In embodiments, the FOXM1 modulator is a pharmaceutically acceptable salt of FDI-2. In embodiments, the FOXM1 modulator is an analog of FDI-2. In embodiments, the FOXM1 modulator is a derivative of FDI-2. In embodiments, the FOXM1 modulator is a prodrug of FDI-2 (e.g., a physiologically hydrolyzable ester thereof or a physiologically hydrolyzable amide thereof). In embodiments, the FOXM1 modulator is FDI-2.

In embodiments, the FOXM1 modulator is "substituted FDI-2." In embodiments of a "substituted FDI-2," an original substituent (e.g., substituent group) of FDI-2 is replaced with an alternative substituent (e.g., substituent group), wherein the alternative substituent (e.g., substituent group) is different from the original substituent (e.g., substituent group). In embodiments of a "substituted FDI-2," a plurality of original substituents (e.g., substituent groups) of FDI-2 are replaced with a plurality of alternative substituents (e.g., substituent groups), wherein the alternative substituents (e.g., substituent groups) are each optionally different and each alternative substituent (e.g., sub stituent group) is different from the original substituent (e.g., substituent group) it replaces. In embodiments of a "substituted FDI-2," a hydrogen atom of FDI-2 is replaced with a substituent (e.g., substituent group). In embodiments of a "substituted FDI-2," a plurality of hydrogen atoms of FDI-2 are replaced with a plurality of substituents (e.g., substituent groups), wherein the substituents (e.g., substituent groups) are each optionally different. In embodiments, the substituent group is a size-limited substituent group. In embodiments, the substituent group is a lower substituent group. The terms "substituent group" and "substituent" are interchangeable and defined herein. It is within the skill in the art of synthetic chemistry to modify FDI-2 to prepare a substituted FDI-2, and it is within the skill in the art to test a substituted FDI-2 to determine whether a substituted FDI-2 can be successfully used in the methods described herein by following the examples herein.

In embodiments, the FOXM1 modulator is FDI-4:

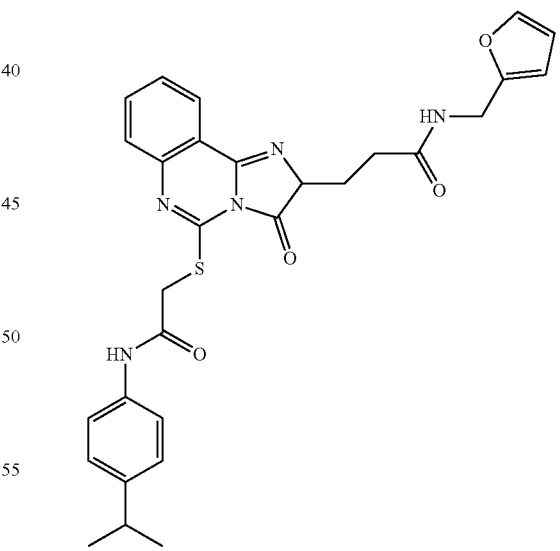

(FDI-4, NCGC00138338) or a derivative, an analog, or a prodrug thereof, or a pharmaceutically acceptable salt of any of the foregoing. In embodiments, the FOXM1 modulator is a pharmaceutically acceptable salt of FDI-4. In embodiments, the FOXM1 modulator is an analog of FDI-4. In embodiments, the FOXM1 modulator is a derivative of FDI-4. In embodiments, the FOXM1 modulator is a prodrug of FDI-4 (e.g., a physiologically hydrolyzable ester thereof or a physiologically hydrolyzable amide thereof). In embodiments, the FOXM1 modulator is FDI-4.

In embodiments, the FOXM1 modulator is a "substituted FDI-4." In embodiments of a "substituted FDI-4," an original substituent (e.g., substituent group) of FDI-4 is replaced with an alternative substituent (e.g., substituent group), wherein the alternative substituent (e.g., substituent group) is different from the original substituent (e.g., substituent group). In embodiments of a "substituted FDI-4," a plurality of original substituents (e.g., substituent groups) of FDI-4 are replaced with a plurality of alternative substituents (e.g., substituent groups), wherein the alternative substituents (e.g., substituent groups) are each optionally different and each alternative substituent (e.g., sub stituent group) is different from the original substituent (e.g., substituent group) it replaces. In embodiments of a "substituted FDI-4," a hydrogen atom of FDI-4 is replaced with a substituent (e.g., substituent group). In embodiments of a "substituted FDI-4," a plurality of hydrogen atoms of FDI-4 are replaced with a plurality of substituents (e.g., substituent groups), wherein the substituents (e.g., substituent groups) are each optionally different. In embodiments, the substituent group is a size-limited substituent group. In embodiments, the substituent group is a lower substituent group. The terms "substituent group" and "substituent" are interchangeable and defined herein. It is within the skill in the art of synthetic chemistry to modify FDI-4 to prepare a substituted FDI-4, and it is within the skill in the art to test a substituted FDI-4 to determine whether a substituted FDI-4 can be successfully used in the methods described herein by following the examples herein.

In embodiments, the FOXM1 modulator is FDI-6:

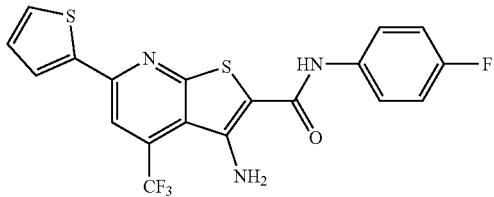 [SMILES: Nc1c(C(=O)Nc2ccc(F)cc2)sc2nc(-c3cccs3)cc(C(F)(F)F)c12]

(FDI-6, NCGC00099374) or a derivative, an analog, or a prodrug thereof, or a pharmaceutically acceptable salt of any of the foregoing. In embodiments, the FOXM1 modulator is a pharmaceutically acceptable salt of FDI-6. In embodiments, the FOXM1 modulator is an analog of FDI-6. In embodiments, the FOXM1 modulator is a derivative of FDI-6. In embodiments, the FOXM1 modulator is a prodrug of FDI-6 (e.g., a physiologically hydrolyzable ester thereof or a physiologically hydrolyzable amide thereof). In embodiments, the FOXM1 modulator is FDI-6.

In embodiments, the FOXM1 modulator is a "substituted FDI-6." In embodiments of a "substituted FDI-6," an original substituent (e.g., substituent group) of FDI-6 is replaced with an alternative substituent (e.g., substituent group), wherein the alternative substituent (e.g., substituent group) is different from the original substituent (e.g., substituent group). In embodiments of a "substituted FDI-6," a plurality of original substituents (e.g., substituent groups) of FDI-6 are replaced with a plurality of alternative substituents (e.g., substituent groups), wherein the alternative substituents (e.g., substituent groups) are each optionally different and each alternative substituent (e.g., sub stituent group) is different from the original substituent (e.g., substituent group) it replaces. In embodiments of a "substituted FDI-6," a hydrogen atom of FDI-6 is replaced with a substituent (e.g., substituent group). In embodiments of a "substituted FDI-6," a plurality of hydrogen atoms of FDI-6 are replaced with a plurality of substituents (e.g., substituent groups), wherein the substituents (e.g., substituent groups) are each optionally different. In embodiments, the substituent group is a size-limited substituent group. In embodiments, the substituent group is a lower substituent group. The terms "substituent group" and "substituent" are interchangeable and defined herein. It is within the skill in the art of synthetic chemistry to modify FDI-6 to prepare a substituted FDI-6, and it is within the skill in the art to test a substituted FDI-6 to determine whether a substituted FDI-6 can be successfully used in the methods described herein by following the examples herein.

In embodiments, the FOXM1 modulator is FDI-7:

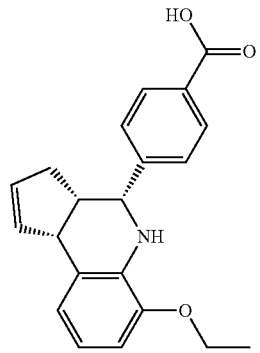 [SMILES: CCOc1cccc2c1N[C@@H](c1ccc(C(=O)O)cc1)[C@H]1CC=C[C@@H]21]

(FDI-7, NCGC00100307) or a derivative, an analog, or a prodrug thereof, or a pharmaceutically acceptable salt of any of the foregoing. In embodiments, the FOXM1 modulator is a pharmaceutically acceptable salt of FDI-7. In embodiments, the FOXM1 modulator is an analog of FDI-7. In embodiments, the FOXM1 modulator is a derivative of FDI-7. In embodiments, the FOXM1 modulator is a prodrug of FDI-7 (e.g., a physiologically hydrolyzable ester thereof or a physiologically hydrolyzable amide thereof). In embodiments, the FOXM1 modulator is FDI-7.

In embodiments, the FOXM1 modulator is a "substituted FDI-7." In embodiments of a "substituted FDI-7," an original substituent (e.g., substituent group) of FDI-7 is replaced with an alternative substituent (e.g., substituent group), wherein the alternative substituent (e.g., substituent group) is different from the original substituent (e.g., substituent group). In embodiments of a "substituted FDI-7," a plurality of original substituents (e.g., substituent groups) of FDI-6 are replaced with a plurality of alternative substituents (e.g., substituent groups), wherein the alternative substituents (e.g., substituent groups) are each optionally different and each alternative substituent (e.g., sub stituent group) is different from the original substituent (e.g., substituent group) it replaces. In embodiments of a "substituted FDI-7," a hydrogen atom of FDI-7 is replaced with a substituent (e.g., substituent group). In embodiments of a "substituted FDI-7," a plurality of hydrogen atoms of FDI-7 are replaced with a plurality of substituents (e.g., substituent groups), wherein the substituents (e.g., substituent groups) are each optionally different. In embodiments, the substituent group is a size-limited substituent group. In embodiments, the substituent group is a lower substituent group. The terms "substituent group" and "substituent" are interchangeable and defined herein. It is within the skill in the art of synthetic chemistry to modify FDI-7 to prepare a substituted FDI-7, and it is within the skill in the art to test a substituted FDI-7 to determine whether a substituted FDI-7 can be successfully used in the methods described herein by following the examples herein.

In embodiments, the FOXM1 modulator is FDI-10:

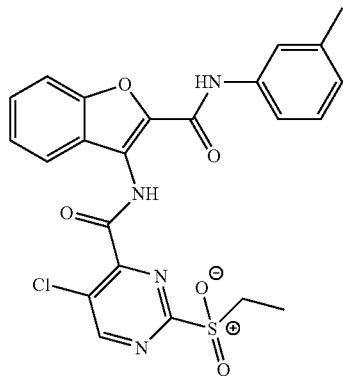 [SMILES: CC[S+](=O)([O-])c1ncc(Cl)c(C(=O)Nc2c(C(=O)Nc3cccc(C)c3)oc3ccccc23)n1]

(FDI-10, NCGC00115080) or a derivative, an analog, or a prodrug thereof, or a pharmaceutically acceptable salt of any of the foregoing. In embodiments, the FOXM1 modulator is a pharmaceutically acceptable salt of FDI-10. In embodiments, the FOXM1 modulator is an analog of FDI-10. In embodiments, the FOXM1 modulator is a derivative of FDI-10. In embodiments, the FOXM1 modulator is a prodrug of FDI-10 (e.g., a physiologically hydrolyzable ester thereof or a physiologically hydrolyzable amide thereof). In embodiments, the FOXM1 modulator is FDI-10.

In embodiments, the FOXM1 modulator is a "substituted FDI-10." In embodiments of a "substituted FDI-10," an original substituent (e.g., substituent group) of FDI-10 is replaced with an alternative substituent (e.g., substituent group), wherein the alternative substituent (e.g., substituent group) is different from the original substituent (e.g., substituent group). In embodiments of a "substituted FDI-10," a plurality of original substituents (e.g., substituent groups) of FDI-10 are replaced with a plurality of alternative substituents (e.g., substituent groups), wherein the alternative substituents (e.g., substituent groups) are each optionally different and each alternative substituent (e.g., sub stituent group) is different from the original substituent (e.g., substituent group) it replaces. In embodiments of a "substituted FDI-10," a hydrogen atom of FDI-10 is replaced with a substituent (e.g., substituent group). In embodiments of a "substituted FDI-10," a plurality of hydrogen atoms of FDI-10 are replaced with a plurality of substituents (e.g., substituent groups), wherein the substituents (e.g., substituent groups) are each optionally different. In embodiments, the substituent group is a size-limited substituent group. In embodiments, the substituent group is a lower substituent group. The terms "substituent group" and "substituent" are interchangeable and defined herein. It is within the skill in the art of synthetic chemistry to modify FDI-10 to prepare a substituted FDI-10, and it is within the skill in the art to test a substituted FDI-10 to determine whether a substituted FDI-10 can be successfully used in the methods described herein by following the examples herein.

In embodiments, the FOXM1 modulator is FDI-11:

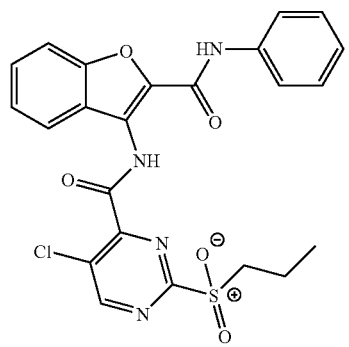 [SMILES: CCC[S+](=O)([O-])c1ncc(Cl)c(C(=O)Nc2c(C(=O)Nc3ccccc3)oc3ccccc23)n1]

(FDI-11, NCGC00115104) or a derivative, an analog, or a prodrug thereof, or a pharmaceutically acceptable salt of any of the foregoing. In embodiments, the FOXM1 modulator is a pharmaceutically acceptable salt of FDI-11. In embodiments, the FOXM1 modulator is an analog of FDI-11. In embodiments, the FOXM1 modulator is a derivative of FDI-11. In embodiments, the FOXM1 modulator is a prodrug of FDI-11 (e.g., a physiologically hydrolyzable ester thereof or a physiologically hydrolyzable amide thereof). In embodiments, the FOXM1 modulator is FDI-11.

In embodiments, the FOXM1 modulator is a "substituted FDI-11." In embodiments of a "substituted FDI-11," an original substituent (e.g., substituent group) of FDI-11 is replaced with an alternative substituent (e.g., substituent group), wherein the alternative substituent (e.g., substituent group) is different from the original substituent (e.g., substituent group). In embodiments of a "substituted FDI-11," a plurality of original substituents (e.g., substituent groups) of FDI-11 are replaced with a plurality of alternative substituents (e.g., substituent groups), wherein the alternative substituents (e.g., substituent groups) are each optionally different and each alternative substituent (e.g., sub stituent group) is different from the original substituent (e.g., substituent group) it replaces. In embodiments of a "substituted FDI-11," a hydrogen atom of FDI-11 is replaced with a substituent (e.g., substituent group). In embodiments of a "substituted FDI-11," a plurality of hydrogen atoms of FDI-11 are replaced with a plurality of substituents (e.g., substituent groups), wherein the substituents (e.g., substituent groups) are each optionally different. In embodiments, the substituent group is a size-limited substituent group. In embodiments, the substituent group is a lower substituent group. The terms "substituent group" and "substituent" are interchangeable and defined herein. It is within the skill in the art of synthetic chemistry to modify FDI-11 to prepare a substituted FDI-11, and it is within the skill in the art to test a substituted FDI-11 to determine whether a substituted FDI-11 can be successfully used in the methods described herein by following the examples herein.

In embodiments, the FOXM1 modulator is siomycin or an analog, derivative, or prodrug thereof (e.g., physiologically hydrolyzable ester), or a pharmaceutically acceptable salt of any of the foregoing. In embodiments, the FOXM1 modulator is siomycin (also known as Siomycin A). In embodiments, the FOXM1 modulator is a "substituted siomycin." In embodiments of a "substituted siomycin," an original substituent (e.g., substituent group) of siomycin is replaced with an alternative substituent (e.g., substituent group), wherein the alternative substituent (e.g., substituent group)

is different from the original substituent (e.g., substituent group). In embodiments of a "substituted siomycin," a plurality of original substituents (e.g., substituent groups) of siomycin are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of "substituted siomycin," a hydrogen atom of siomycin is replaced with a substituent (e.g., substituent group). In embodiments of "substituted siomycin," a plurality of hydrogen atoms of siomycin are replaced with a plurality of substituents (e.g., substituent groups), wherein the substituents (e.g., substituent groups) are each optionally different. In embodiments, the substituent group is a size-limited substituent group. In embodiments, the substituent group is a lower substituent group. The terms "substituent group" and "substituent" are interchangeable and defined herein. It is within the skill in the art of synthetic chemistry to modify siomycin to prepare a substituted siomycin, and it is within the skill in the art to test a substituted siomycin to determine whether a substituted siomycin can be successfully used in the methods described herein by following the examples herein.

In embodiments, the FOXM1 modulator is thiostrepton or an analog, derivative, or prodrug thereof (e.g., physiologically hydrolyzable ester), or a pharmaceutically acceptable salt of any of the foregoing. In embodiments, the FOXM1 modulator is thiostrepton. In embodiments, thiostrepton is a "substituted thiostrepton." In embodiments of a "substituted thiostrepton," an original substituent (e.g., substituent group) of thiostrepton is replaced with an alternative substituent (e.g., substituent group), wherein the alternative substituent (e.g., substituent group) is different from the original substituent (e.g., substituent group). In embodiments of a "substituted thiostrepton," a plurality of original substituents (e.g., substituent groups) of thiostrepton are replaced with a plurality of alternative substituents (e.g., substituent groups), wherein the alternative substituents (e.g., substituent groups) are each optionally different and each alternative substituent (e.g., sub stituent group) is different from the original substituent (e.g., substituent group) it replaces. In embodiments of a "substituted thiostrepton," a hydrogen atom of thiostrepton is replaced with a substituent (e.g., substituent group). In embodiments of a "substituted thiostrepton," a plurality of hydrogen atoms of thiostrepton are replaced with a plurality of substituents (e.g., substituent groups), wherein the substituents (e.g., substituent groups) are each optionally different. In embodiments, the substituent group is a size-limited substituent group. In embodiments, the substituent group is a lower substituent group. The terms "substituent group" and "substituent" are interchangeable and defined herein. It is within the skill in the art of synthetic chemistry to modify thiostrepton to prepare a substituted thiostrepton, and it is within the skill in the art to test a substituted thiostrepton to determine whether a substituted thiostrepton can be successfully used in the methods described herein by following the examples herein.

In embodiments, the FOXM1 modulator is a thiazole antibiotic selected from 68-1147, A10255, A-8506, amythiamicin, berninamycin, bryamycin, cyclothiazomycin, GE2270, GE37468, geninthiocin, glycothiohexide, JBIR-83-4, methylsulfonycin, micrococcin, MJ347-81F4, multhiomycin, neoberninamycin, nocardithiocin, nocathiacin, nosiheptide, promoinducin, promothiocin, QN3323, radamycin, S-54832, Sch 18640, Sch 40832, siomycin, sulfomycin, thiactin, thioactin, thiocillin, thiomuracins, thiopeptin, thiostrepton, thiotipin, thioxamycin, TP-1161, and YM-266183-4, or an analog, derivative, or prodrug of any one of the foregoing. In embodiments, the FOXM1 modulator is a thiazole antibiotic selected from BMS-249524, BMS-461996, and BMS-411886, or an analog, derivative, or prodrug (e.g., physiologically hydrolyzable ester) of any one of the foregoing, as described in Pucci et al, Antimicrobial Agents and Chemotherapy, 48(10):3697-3701 (2004), which is incorporated herein by reference in its entirety for any purpose. In embodiments of any of the foregoing, any of the antibiotics can be a "substituted thiazole antibiotic." In embodiments of a "substituted thiazole antibiotic," an original substituent (e.g., substituent group) of a thiazole antibiotic is replaced with an alternative substituent (e.g., substituent group), wherein the alternative substituent (e.g., substituent group) is different from the original substituent (e.g., substituent group). In embodiments of a "substituted thiazole antibiotic," a plurality of original substituents (e.g., substituent groups) of a thiazole antibiotic are replaced with a plurality of alternative substituents (e.g., substituent groups), wherein the alternative substituents (e.g., substituent groups) are each optionally different and each alternative substituent (e.g., sub stituent group) is different from the original substituent (e.g., substituent group) it replaces. In embodiments of a "substituted thiazole antibiotic," a hydrogen atom of a thiazole antibiotic is replaced with a substituent (e.g., substituent group). In embodiments of a "substituted thiazole antibiotic," a plurality of hydrogen atoms of a thiazole antibiotic are replaced with a plurality of substituents (e.g., substituent groups), wherein the substituents (e.g., substituent groups) are each optionally different. In embodiments, the substituent group is a size-limited substituent group. In embodiments, the substituent group is a lower substituent group. The terms "substituent group" and "substituent" are interchangeable and defined herein. It is within the skill in the art of synthetic chemistry to modify thiazole antibiotics to prepare a substituted thiazole antibiotic, and it is within the skill in the art to test a substituted thiazole antibiotic to determine whether a substituted thiazole antibiotic can be successfully used in the methods described herein by following the examples herein.

In embodiments, the FOXM1 modulator decreases the level of FOXM1 activity (e.g., compared to control). In embodiments, the FOXM1 modulator decreases the level of androgen receptor activity (e.g., compared to control). In embodiments, the FOXM1 modulator decreases the level of androgen receptor activity in a neuron (e.g., compared to control). In embodiments, the FOXM1 modulator decreases the level of androgen receptor activity in a motor neuron (e.g., compared to control). In embodiments, the FOXM1 modulator decreases the level of androgen receptor activity in a motor neuron more than the level of androgen receptor activity in a myocyte (e.g. myocyte innervated by the motor neuron). In embodiments, the FOXM1 modulator decreases (e.g., compared to control) the level of androgen receptor activity in a motor neuron more than the level of androgen receptor activity in a muscle cell (e.g. muscle cell innervated by the motor neuron). In embodiments, a control is the same experiment without administration of the FOXM1 modulator. In embodiments, the FOXM1 modulator decreases (e.g., compared to control) the level of androgen receptor activity in a motor neuron more than the level of androgen receptor activity in a myocyte (e.g. myocyte innervated by the motor neuron) by a factor of about 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000-fold. In embodiments, the FOXM1 modulator decreases (e.g., compared to control) the level of androgen receptor activity in a motor neuron more than the level of androgen receptor activity in a myocyte (e.g. myocyte innervated by the motor neuron) by a factor of 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000-fold. In embodiments, the FOXM1 modulator decreases (e.g., compared to control) the level of androgen receptor activity in a motor neuron more than the level of androgen receptor activity in a myocyte (e.g. myocyte innervated by the motor neuron) by a factor of at least 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000-fold. In embodiments, the FOXM1 modulator decreases the level of androgen receptor activity in a motor neuron but not the level of androgen receptor activity in a myocyte (e.g. myocyte innervated by the motor neuron) at the same concentration of FOXM1 modulator.

In embodiments, the FOXM1 modulator (e.g., inhibitor) reduces the level of FOXM1 activity in a motor neuron compared to control (e.g., by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In embodiments, the FOXM1 modulator (e.g., inhibitor) binds FOXM1 protein with a Kd (dissociation constant) of less than (i.e. stronger binding affinity) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, or 1000000 picomolar (pM). In embodiments, the FOXM1 modulator (e.g., inhibitor) reduces the level of FOXM1 activity with an IC50 of less than (i.e. stronger inhibition) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, or 1000000 picomolar (pM). In embodiments, the FOXM1 modulator (e.g., inhibitor) reduces the level of FOXM1 protein in a motor neuron compared to control (e.g., by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%).

In embodiments, the FOXM1 modulator (e.g., inhibitor) reduces the level of activity of androgen receptor in a motor neuron compared to control. In embodiments, the androgen receptor includes an expanded polyglutamine tract compared to wildtype androgen receptor.

In embodiments, the FOXM1 modulator (e.g., inhibitor) is a peptide including SEQ ID NO:5. In embodiments, the FOXM1 modulator (e.g., inhibitor) is a peptide including SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18; SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27; SEQ ID NO:28, SEQ ID NO:29, SEQ ID NO:30, SEQ ID NO: 31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, or SEQ ID NO:40. In embodiments, the FOXM1 modulator (e.g., inhibitor) is a peptide including SEQ ID NO:3. In embodiments, the FOXM1 modulator (e.g., inhibitor) is a peptide including SEQ ID NO:4. In embodiments, the FOXM1 modulator (e.g., inhibitor) reduces the interaction between FOXM1 and androgen receptor in a motor neuron. In embodiments, the FOXM1 modulator (e.g., inhibitor) reduces the interaction between FOXM1 and androgen receptor in a motor neuron (e.g., by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In embodiments, the FOXM1 modulator (e.g., inhibitor) reduces the level of FOXM1 and androgen receptor complex in a motor neuron (e.g., by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%).

In embodiments, the FOXM1 modulator (e.g., inhibitor) reduces the interaction between FOXM1 and β-catenin in the motor neuron. In embodiments, the FOXM1 modulator (e.g., inhibitor) reduces the interaction between FOXM1 and β-catenin in the motor neuron (e.g., by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%).

In embodiments, the FOXM1 modulator (e.g., inhibitor) reduces the level of a FOXM1/androgen receptor/β-catenin complex in the motor neuron. In embodiments, the FOXM1 modulator (e.g., inhibitor) reduces the level of a FOXM1/androgen receptor/β-catenin complex in the motor neuron compared to control (e.g., by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%).

Pharmaceutical Compositions

The disclosure provides pharmaceutical compositions including a pharmaceutically acceptable excipient and a FOXM1 modulator (e.g., inhibitor) or pharmaceutically acceptable salt thereof (e.g., as described herein). In embodiments of the pharmaceutical compositions, the FOXM1 modulator (e.g., inhibitor), or pharmaceutically acceptable salt thereof, is included in a therapeutically effective amount.

In embodiments, the pharmaceutical composition includes a second agent (e.g. therapeutic agent). In embodiments, the pharmaceutical composition includes a second agent (e.g. therapeutic agent) in a therapeutically effective amount. In embodiments, the second agent is an agent for treating spinal-bulbar muscular atrophy or an aberrant level of androgen receptor activity or a disease associated with androgen receptor activity. In embodiments, the second agent is an anti-androgen receptor agent. In embodiments, the second agent is a chemotherapeutic. In embodiments, the second agent is an anti-prostate cancer agent. In embodiments, the second agent is an agent for treating hormone-sensitive prostate cancer. In embodiments, the second agent is an agent for treating hormone-insensitive prostate cancer. In embodiments, the second agent binds androgen receptor at the hormone binding site. In embodiments, the second agent is flutamide. In embodiments, the second agent is bicalutamide. In embodiments, the second agent is nilutamide. In embodiments, the second agent is enzalutamide. In embodiments, the second agent is ARN-509. In embodiments, the second agent binds androgen receptor at a site that is not the hormone binding site. In embodiments, the second agent is a luteinizing hormone-releasing hormone analogue (LHRH analogue or analog). In embodiments, the second agent is a luteinizing hormone-releasing hormone agonist. In embodiments, the second agent is a luteinizing hormone-releasing hormone analogue antagonist. In embodiments, the second agent is a gonadotropin-releasing hormone analogue (GnRH analogue or analog). In embodiments, the second agent is a gonadotropin-releasing hormone agonist. In embodiments, the second agent is a gonadotropin-releasing hormone analogue antagonist. In embodiments, the second agent is leuprolide, goserelin, triptorelin, hisrelin, degarelix, or abiraterone. A luteinizing hormone-releasing hormone analogue or gonadotropin-releasing hormone analogue is a composition (e.g., peptide) that interacts with (binds) the GnRH receptor and modulates the release of pituitary gonadotropins follicle-stimulating hormone and/or luteinizing hormone. In embodiments, the second agent is avorelin, buserelin, deslorelin, gonadorelin, goserelin, histrelin, leuprorelin, lutrelin, nafarelin, peforelin, or triptorelin. In embodiments, the second agent is abarelix, cetrorelix, degarelix, detirelix, ganirelix, iturelix, oxarelix, prazarelix, ramorelix, or teverelix. In embodiments, the second agent is casodex. In embodiments, the second agent is abiraterone. In embodiments, the second agent is abiraterone acetate. In embodiments, the second agent is an inhibitor of androgen synthesis. In embodiments, the second agent is an inhibitor of CYP17A1. In embodiments, the second agent is cyproterone acetate. In embodiments, the second agent is orteronel. In embodiments, the second agent is VT-464. In embodiments, the second agent is galeterone. In embodiments, the second agent is an agent for treating Alzheimer's Disease. In embodiments, the second agent is a cholinesterase inhibitor. In embodiments, the second agent is donepezil. In embodiments, the second agent is rivastigmine. In embodiments, the second agent is galantamine. In embodiments, the second agent is memantine. In embodiments, the second agent is an agent for treating amyotrophic lateral sclerosis (ALS). In embodiments, the second agent is riluzole (Rilutek). In embodiments, the second agent is dexpramipexole. In embodiments, the second agent is ceftriaxone. In embodiments, the second agent is CK2017357 (Tirasemtiv). In embodiments, the second agent is NP001. In embodiments, the second agent is Copper-ATSM.

Methods of Treatment

The disclosure provides methods to treat diseases associated with androgen receptor activity by administering FOXM1 modulators, such as a FOXM1 inhibitor. The disclosure provides methods described to treat diseases associated with androgen receptor activity (i.e., an androgen receptor activity-associated disease) by inhibiting androgen receptor activity by administering FOXM1 modulators, such as a FOXM1 inhibitor. Exemplary diseases associated with androgen receptor activity include prostate cancer, benign prostatic hyperplasia, hypersexuality, acne, amenorrhea, seborrhea, hirsutism, androgenic alopecia, hidradenitis suppurativa, spinal-bulbar muscular atrophy, Alzheimer's disease, amyotrophic lateral sclerosis, and hyperandrogenism. The disclosure provides methods to treat prostate cancer, benign prostatic hyperplasia, hypersexuality, acne, amenorrhea, seborrhea, hirsutism, androgenic alopecia, hidradenitis suppurativa, spinal-bulbar muscular atrophy, Alzheimer's Disease, amyotrophic lateral sclerosis, and hyperandrogenism in a subject in need by administering a FOXM1 modulator, such as a FOXM1 inhibitor. The methods described herein may treat diseases associated with androgen receptor activity by inhibiting coactivator or transcriptional proteins from binding to androgen receptor. The FOXM1 inhibitors will be administered in therapeutically effective amounts.

The disclosure provides methods to treat spinal-bulbar muscular atrophy by administering a FOXM1 inhibitor, as described herein. In embodiments, the methods of treating spinal-bulbar muscular atrophy are methods of treating a symptom of spinal-bulbar muscular atrophy. Methods of treating a symptom include alleviating a symptom of spinal-bulbar muscular atrophy, e.g., the symptom will become less severe, the symptom will become less frequent, the symptom will be eliminated, or a combination thereof. In embodiments, the methods of treating spinal-bulbar muscular atrophy are methods of delaying the onset of spinal-bulbar muscular atrophy. "Delaying the onset of spinal-bulbar muscular atrophy" means that (i) an existing symptom of SBMA in a subject will take longer to worsen; (ii) the onset of a new symptom will be prevented or delayed; (iii) a patient will experience fewer symptoms of SBMA over time; or (v) a combination of the foregoing. "Delaying the onset" may be in reference to a patient who is not taking a FOXM1 inhibitor as described herein or in reference to the statistically normal progression of the disease. Symptoms of spinal-bulbar muscular atrophy include muscle weakness (e.g., arms, legs); muscle cramping (e.g., arms legs); muscle twitching (e.g., arm, legs); muscle atrophy (e.g., arms, legs); difficulty speaking; difficulty chewing; difficulty swallowing; difficulty breathing during sleep; difficulty conveying facial expressions. In addition or alternatively, the symptoms of spinal-bulbar muscular atrophy can be hormonal, such as gynecomastia, reduced fertility, and testicular atrophy.

The disclosure provides methods to treat amyotrophic lateral sclerosis by administering a FOXMI inhibitor, as described herein. In embodiments, the methods of treating amyotrophic lateral sclerosis include treating a symptom of amyotrophic lateral sclerosis and/or slowing the progression of one or more symptoms of amyotrophic lateral sclerosis. Exemplary symptoms of amyotrophic lateral sclerosis include muscle weakness (e.g., arms, legs, hands, feet); muscle atrophy (e.g., arms, legs, hands feet); muscle cramping (e.g., arms, legs, hands, feet); muscle twitching (e.g., arms, legs, hands, feet); difficulty speaking; difficulty swallowing; and difficulty breathing.

The disclosure provides methods to treat Alzheimer's Disease by administering a FOXMI inhibitor, as described herein. In embodiments, the methods of treating Alzheimer's disease include decreasing one or more symptoms of Alzheimer's Disease and/or slowing the progression of one or more symptoms of Alzheimer's Disease. Symptoms of Alzheimer's include difficulty speaking; difficulty conveying facial expression; difficulty walking; muscle tremors; and muscle rigidity.

In embodiments, the method includes administering a second agent (e.g. therapeutic agent). In embodiments, the method includes administering a second agent (e.g. therapeutic agent) in a therapeutically effective amount. In embodiments of the methods, the second agent is an agent for treating spinal-bulbar muscular atrophy or an aberrant level of androgen receptor activity or a disease associated with androgen receptor activity (e.g., spinal-bulbar muscular atrophy). In embodiments, the second agent is an anti-androgen receptor agent. In embodiments, the second agent is a chemotherapeutic. In embodiments, the second agent is an anti-prostate cancer agent. In embodiments, the second agent is an agent for treating hormone-sensitive prostate cancer. In embodiments, the second agent is an agent for treating hormone-insensitive prostate cancer. In embodiments, the second agent binds androgen receptor at a site that includes the hormone binding site. In embodiments, the second agent binds androgen receptor at the hormone binding site. In embodiments, the second agent is flutamide. In embodiments, the second agent is bicalutamide. In embodiments, the second agent is nilutamide. In embodiments, the second agent is enzalutamide. In embodiments, the second agent is ARN-509. In embodiments, the second agent binds androgen receptor at a site that does not include the hormone binding site. In embodiments, the second agent binds androgen receptor at a site that does is not the hormone binding site. In embodiments, the second agent is an agent for treating Alzheimer's Disease. In embodiments, the second agent is a cholinesterase inhibitor. In embodiments, the second agent is donepezil. In embodiments, the second agent is rivastigmine. In embodiments, the second agent is galantamine. In embodiments, the second agent is memantine. In embodiments, the second agent is an agent for treating amyotrophic lateral sclerosis. In embodiments, the second agent is riluzole (Rilutek). In embodiments, the second agent is dexpramipexole. In embodiments, the second agent is ceftriaxone. In embodiments, the second agent is CK2017357 (also known as tirasemtiv). In embodiments, the second agent is NP001. In embodiments, the second agent is Copper-ATSM.

The disclosure provides a FOXM1 modulator (e.g., as described herein) for use in the treatment of an androgen receptor activity-associated disease in a subject in need of such treatment. The use may include administering a FOXM1 modulator (e.g., as described herein), or a pharmaceutically acceptable salt thereof. The disclosure provides a FOXM1 modulator (e.g., as described herein) for use in the treatment of spinal-bulbar muscular atrophy. The use may include administering a FOXM1 modulator (e.g., as described herein), or a pharmaceutically acceptable salt thereof. In embodiments, the FOXM1 modulator is administered in a therapeutically effective amount. The disclosure provides a FOXM1 modulator (e.g., as described herein) for use in the treatment of Alzheimer's Disease. The use may include administering a FOXM1 modulator (e.g., as described herein), or a pharmaceutically acceptable salt thereof. In embodiments, the FOXM1 modulator is administered in a therapeutically effective amount. The disclosure provides a FOXM1 modulator (e.g., as described herein) for use in the treatment of amyotrophic lateral sclerosis (ALS). The use may include administering a FOXM1 modulator (e.g., as described herein), or a pharmaceutically acceptable salt thereof. In embodiments, the FOXM1 modulator is administered in a therapeutically effective amount. The disclosure provides a method of inhibiting androgen receptor activity in a subject in need thereof, including administering to the subject an effective amount of a FOXM1 modulator (e.g., as described herein), or a pharmaceutically acceptable salt thereof. The disclosure provides a FOXM1 modulator (e.g., as described herein) for use as a medicament. The disclosure provides the use of a FOXM1 modulator (e.g., as described herein) in the manufacture of a medicament for the treatment of an androgen receptor activity-associated disease in a subject in need of such treatment. The use may include administering a FOXM1 modulator (e.g., as described herein), or a pharmaceutically acceptable salt thereof. In embodiments, the FOXM1 modulator, or pharmaceutically acceptable salt thereof, is included in an effective amount. In embodiments, the FOXM1 modulator, or pharmaceutically acceptable salt thereof, is included in a therapeutically effective amount. In embodiments, the FOXM1 modulator, or pharmaceutically acceptable salt thereof, is included in a prophylactically effective amount. In embodiments, the treatment is prevention. In embodiments, the FOXM1 modulators (e.g., as described herein) are provided as pharmaceutical compositions including the FOXM1 modulator and a pharmaceutically acceptable excipient.

The disclosure provides a method of treating spinal-bulbar muscular atrophy in a subject in need of such treatment, the method including administering a FOXM1 modulator (e.g., as described herein), or a pharmaceutically acceptable salt thereof, including embodiments or in an example, table, figure, or claim. The disclosure provides a method of treating Alzheimer's Disease in a subject in need of such treatment, the method including administering a FOXM1 modulator (e.g., as described herein), or a pharmaceutically acceptable salt thereof, including embodiments or in an example, table, figure, or claim. The disclosure provides a method of treating amyotrophic lateral sclerosis (ALS) in a subject in need of such treatment, the method including administering a FOXM1 modulator (e.g., as described herein), or a pharmaceutically acceptable salt thereof, including embodiments or in an example, table, figure, or claim.

In embodiments, the FOXM1 modulator (e.g., inhibitor) reduces the level of FOXM1 activity in a motor neuron compared to control (e.g., by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%). In embodiments, the FOXM1 modulator (e.g., inhibitor) reduces the level of FOXM1 protein in a motor neuron compared to control (e.g., by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%).

In embodiments, the FOXM1 modulator (e.g., inhibitor) reduces the level of activity of androgen receptor in a motor neuron compared to control. In embodiments, the androgen receptor includes an expanded polyglutamine tract compared to wildtype androgen receptor.

The disclosure provides a method of reducing the level of androgen receptor activity in a motor neuron compared to control (e.g., by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%), the method including contacting the motor neuron with an effective amount of a FOXM1 modulator (e.g., inhibitor, as described herein).

In embodiments, the androgen receptor includes an expanded polyglutamine tract compared to wildtype androgen receptor (e.g., expanded by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 Q compared to control (e.g., wildtype, non-disease associated androgen receptor). In embodiments, the FOXM1 modulator (e.g., inhibitor) is an antibiotic. In embodiments, the antibiotic is a thiazole antibiotic. In embodiments, the antibiotic is thiostrepton or siomycin A. In embodiments, the FOXM1 modulator (e.g., inhibitor) is FDI-2, FDI-4, FDI-6, FDI-7, FDI-10, or FDI-11. In embodiments, the FOXM1 modulator (e.g., inhibitor) is a peptide having a sequence at least 80% (e.g., 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9, or 100%) identical to a portion of human p14ARF protein, or at least 80% identical to SEQ ID NO:3. In embodiments, the FOXM1 modulator (e.g., inhibitor) is a peptide having a sequence at least 80% (e.g., 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9, or 100%) identical to a portion of mouse p19ARF protein or at least 80% identical to SEQ ID NO:4.

In embodiments, the FOXM1 modulator (e.g., inhibitor) is a peptide including SEQ ID NO:5. In embodiments, the FOXM1 modulator (e.g., inhibitor) is a peptide including SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18; SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27; SEQ ID NO:28, SEQ ID NO:29, SEQ ID NO:30, SEQ ID NO: 31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, or SEQ ID NO:40. In embodiments, the FOXM1 modulator (e.g., inhibitor) reduces the interaction between FOXM1 and androgen receptor in the motor neuron. In embodiments, the FOXM1 modulator (e.g., inhibitor) reduces the interaction between FOXM1 and androgen receptor in the motor neuron (e.g., by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%).

In embodiments, the FOXM1 modulator (e.g., inhibitor) reduces the interaction between FOXM1 and β-catenin in the motor neuron. In embodiments, the FOXM1 modulator (e.g., inhibitor) reduces the interaction between FOXM1 and β-catenin in the motor neuron (e.g., by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%).

In embodiments, the FOXM1 modulator (e.g., inhibitor) reduces the level of a FOXM1/androgen receptor/β-catenin complex in the motor neuron. In embodiments, the FOXM1 modulator (e.g., inhibitor) reduces the level of a FOXM1/androgen receptor/β-catenin complex in the motor neuron compared to control (e.g., by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%).

The disclosure provides a method of increasing the survival of a motor neuron (e.g., by at least an average of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, or 5000 days) including contacting the motor neuron with a FOXM1 modulator (e.g., as described herein, a FOXM1 inhibitor).

The disclosure provides a method of reducing muscle atrophy (e.g., by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) including contacting a motor neuron innervating the muscle with a FOXM1 modulator (e.g., as described herein, a FOXM1 inhibitor). The disclosure provides a method of slowing muscle atrophy (e.g., by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, or 10000 days) including contacting a motor neuron innervating the muscle with a FOXM1 modulator (e.g., as described herein, a FOXM1 inhibitor).

Methods of Inhibiting an Androgen Receptor

The disclosure provides a method of inhibiting androgen receptor activity in a subject in need thereof, including administering to the subject an effective amount of a FOXM1 modulator (e.g., as described herein), or a pharmaceutically acceptable salt thereof.

The disclosure provides a method of inhibiting androgen receptor activity, the method including contacting a FOXM1 protein with an effective amount of a FOXM1 modulator described herein, or a pharmaceutically acceptable salt thereof.

In embodiments, the method decreases the level of androgen receptor activity (e.g., compared to control). In embodiments, the method decreases the level of androgen receptor activity in a neuron (e.g., compared to control). In embodiments, the method decreases the level of androgen receptor activity in a motor neuron (e.g., compared to control). In embodiments, the method decreases the level of androgen receptor activity in a motor neuron more than the level of androgen receptor activity in a myocyte (e.g. myocyte innervated by the motor neuron). In embodiments, the method decreases (e.g., compared to control) the level of androgen receptor activity in a motor neuron more than the level of androgen receptor activity in a muscle cell (e.g. muscle cell innervated by the motor neuron). In embodiments, a control is the same experiment without administration of the FOXM1 modulator. In embodiments, the method decreases (e.g., compared to control) the level of androgen receptor activity in a motor neuron more than the level of androgen receptor activity in a myocyte (e.g. myocyte innervated by the motor neuron) by a factor of about 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000-fold. In embodiments, the method decreases (e.g., compared to control) the level of androgen receptor activity in a motor neuron more than the level of androgen receptor activity in a myocyte (e.g. myocyte innervated by the motor neuron) by a factor of 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000-fold. In embodiments, the method decreases (e.g., compared to control) the level of androgen receptor activity in a motor neuron more than the level of androgen receptor activity in a myocyte (e.g. myocyte innervated by the motor neuron) by a factor of at least 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000-fold. In embodiments, the method decreases the level of androgen receptor activity in a motor neuron but not level of androgen receptor activity in a myocyte (e.g. myocyte innervated by the motor neuron) at the same concentration of FOXM1 modulator.

Methods of Inhibiting FOXM1

The disclosure provides a method of inhibiting FOXM1 activity in a subject in need thereof, including administering to the subject an effective amount of a FOXM1 modulator as described herein, or a pharmaceutically acceptable salt thereof.

The disclosure provides a method of inhibiting FOXM1 activity, the method including contacting a FOXM1 protein with an effective amount of a FOXM1 modulator described herein, or a pharmaceutically acceptable salt thereof.

The disclosure provides a method of reducing the level of FOXM1 activity in a neuron (e.g., motor neuron), the method including contacting the neuron (e.g., motor neuron) with an effective amount of a FOXM1 modulator described herein, or a pharmaceutically acceptable salt thereof. In embodiments, the FOXM1 modulator decreases the level of expression of FOXM1.

EMBODIMENTS

Embodiment 1

A method of treating spinal-bulbar muscular atrophy in a subject in need thereof, the method comprising administering to the subject a therapeutically effective amount of a FOXM1 inhibitor to treat the spinal-bulbar muscular atrophy.

Embodiment 2

The method of embodiment 1, wherein the administering comprises contacting a motor neuron of the subject with the FOXM1 inhibitor Embodiment 3

The method of embodiment 1 or 2, wherein the method of treating spinal-bulbar muscular atrophy comprises a method of treating a symptom of spinal-bulbar muscular atrophy.

Embodiment 4

The method of embodiment 1, 2, or 3, wherein the method of treating spinal-bulbar muscular atrophy comprises delaying the onset of spinal-bulbar muscular atrophy.

Embodiment 5

A method of reducing the level of androgen receptor activity in a motor neuron, the method comprising contacting the motor neuron with an effective amount of a FOXM1 inhibitor to reduce the level of androgen receptor activity in the motor neuron.

Embodiment 6

The method of embodiment 5, wherein the androgen receptor comprises an expanded polyglutamine tract compared to a wildtype androgen receptor Embodiment 7

A method of treating an androgen receptor activity-associated disease in a subject in need thereof, the method comprising administering to the subject a therapeutically effective amount of a FOXM1 inhibitor to treat the androgen receptor activity-associated disease.

Embodiment 8

The method of embodiment 7, wherein the androgen receptor activity-associated disease is prostate cancer, benign prostatic hyperplasia, hypersexuality, acne, am enorrhea, seborrhea, hirsutism, androgenic alopecia, hidradenitis suppurativa, spinal-bulbar muscular atrophy, Alzheimer's Disease, amyotrophic lateral sclerosis, or hyperandrogenism.

Embodiment 9

A method of treating amyotrophic lateral sclerosis in a subject in need thereof, the method comprising administering to the subject a therapeutically effective amount of a FOXM1 inhibitor to treat the amyotrophic lateral sclerosis.

Embodiment 10

A method of treating Alzheimer's disease in a subject in need thereof, the method comprising administering to the subject a therapeutically effective amount of a FOXM1 inhibitor to treat the Alzheimer's disease.

Embodiment 11

The method of any one of embodiments 1 to 10, wherein the FOXM1 inhibitor is an antibiotic.

Embodiment 12

The method of any one of embodiments 1 to 10, wherein the FOXM1 inhibitor is a thiazole antibiotic.

Embodiment 13

The method of any one of embodiments 1 to 10, wherein the FOXM1 inhibitor is thiostrepton.

Embodiment 14

The method of any one of embodiments 1 to 10, wherein the FOXM1 inhibitor is siomycin.

Embodiment 15

The method of any one of embodiments 1 to 10, wherein the FOXM1 inhibitor is FDI-2, FDI-4, FDI-6, FDI-7, FDI-10, or FDI-11; or a pharmaceutically acceptable salt of any one of the foregoing.

Embodiment 16

The method of any one of embodiments 1 to 10, wherein the FOXM1 inhibitor is a substituted FDI-2, a substituted FDI-4, a substituted FDI-6, a substituted FDI-7, a substituted FDI-10, a substituted FDI-11, a substituted thiostrepton, or a substituted siomycin; or a pharmaceutically acceptable salt of any of the foregoing Embodiment 17

The method of any one of embodiments 1 to 10, wherein the FOXM1 inhibitor is a peptide comprising a sequence that is at least 80% identical to SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18; SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27; SEQ ID NO:28, SEQ ID NO:29, SEQ ID NO:30, SEQ ID NO: 31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, or SEQ ID NO:40

Embodiment 18

The method of any one of embodiments 1 to 10, wherein the FOXM1 inhibitor is a peptide comprising a sequence that is at least 90% identical to SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18; SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27; SEQ ID NO:28, SEQ ID NO:29, SEQ ID NO:30, SEQ ID NO: 31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, or SEQ ID NO:40.

Embodiment 19

The method of any one of embodiments 1 to 10, wherein the FOXM1 inhibitor is a peptide comprising SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18; SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27; SEQ ID NO:28, SEQ ID NO:29, SEQ ID NO:30, SEQ ID NO: 31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, or SEQ ID NO:40.

Embodiment 20

The method of any one of embodiments 1 to 10, wherein the FOXM1 inhibitor is a peptide comprising a sequence that is at least 80% identical to SEQ ID NO:5.

Embodiment 21

The method of any one of embodiments 1 to 10, wherein the FOXM1 inhibitor is a peptide comprising a sequence that is at least 90% identical to SEQ ID NO:5.

Embodiment 22

The method of any one of embodiments 1 to 10, wherein the FOXM1 inhibitor is a peptide comprising SEQ ID NO:5.

Embodiment 23

The method of any one of embodiments 1 to 10, wherein the FOXM1 inhibitor is a peptide having a sequence at least 80% identical to a portion of human p14ARF protein.

Embodiment 24

The method of any one of claims 1 to 10, wherein the FOXM1 inhibitor is a peptide having a sequence at least 80% identical to a portion of a mouse p19ARF protein.

Embodiment 25

The method of any one of embodiments 1 to 10, wherein the FOXM1 inhibitor is a peptide having a sequence at least 85% identical to SEQ ID NO:3.

Embodiment 26

The method of any one of embodiments 1 to 10, wherein the FOXM1 inhibitor is a peptide having a sequence of SEQ ID NO:3.

Embodiment 27

The method of any one of embodiments 1 to 10, wherein the FOXM1 inhibitor is a peptide having a sequence at least 85% identical to SEQ ID NO:4.

Embodiment 28

The method of any one of embodiments 1 to 10, wherein the FOXM1 inhibitor is a peptide having a sequence of SEQ ID NO:4.

Embodiment 29

The method of any one of embodiments 1 to 28, wherein the FOXM1 inhibitor reduces the interaction between FOXM1 and an androgen receptor in a motor neuron.

Embodiment 30

The method of any one of embodiments 1 to 28, wherein the FOXM1 inhibitor reduces the interaction between FOXM1 and β-catenin in a motor neuron.

Embodiment 31

The method of any one of embodiments 1 to 28, wherein the FOXM1 inhibitor reduces the level of a complex of FOXM1, androgen receptor, and β-catenin in a motor neuron.

Embodiment 32

The method of any one of embodiments 1 to 31, wherein the FOXM1 inhibitor selectively inhibits androgen receptor activity in a neuronal cell.

Embodiment 33

The method of any one of embodiments 1 to 32, wherein the FOXM1 inhibitor selectively inhibits androgen receptor activity in a neuronal cell in comparison to a muscle cell.

Embodiment 34

The method of any one of embodiments 1 to 33, wherein the FOXM1 inhibitor does not inhibit androgen receptor activity in a muscle cell.

Embodiments—P

Embodiment P1

A method of treating spinal-bulbar muscular atrophy (SBMA) in a subject in need of such treatment, said method comprising administering to the subject a therapeutically effective amount of a FOXM1 inhibitor.

Embodiment P2

The method of embodiment P1, comprising contacting a motor neuron of the subject with an effective amount of the FOXM1 inhibitor.

Embodiment P3

The method of embodiment P1, comprising preventing atrophy of a motor neuron of the subject compared to control.

Embodiment P4

The method of embodiment P1, comprising reducing atrophy of a motor neuron of the subject compared to control.

Embodiment P5

The method of any one of embodiments P2 to P4, wherein the motor neuron innervates a spinal muscle.

Embodiment P6

The method of any one of embodiments P2 to P4, wherein the motor neuron innervates a bulbar muscle.

Embodiment P7

A method of reducing the level of androgen receptor activity in a motor neuron compared to control, said method comprising contacting the motor neuron with an effective amount of a FOXM1 inhibitor.

Embodiment P8

The method of embodiment P7, wherein the androgen receptor comprises an expanded polyglutamine tract compared to wildtype androgen receptor.

Embodiment P9

The method of any one of embodiments P1 to P8, wherein the FOXM1 inhibitor is an antibiotic.

Embodiment P10

The method of embodiment P9, wherein the antibiotic comprises a thiazolyl (e.g., a thiazole antibiotic).

Embodiment P11

The method of embodiment P9, wherein the antibiotic is thiostrepton or siomycin A.

Embodiment P12

The method of any one of embodiments P1 to P8, wherein the FOXM1 inhibitor is FDI-2, FDI-4, FDI-6, FDI-7, FDI-10, or FDI-11.

Embodiment P13

The method of any one of embodiments P1 to P8, wherein the FOXM1 inhibitor is a peptide having a sequence at least 80% identical to a portion of human p14ARF protein.

Embodiment P14

The method of any one of embodiments P1 to P8, wherein the FOXM1 inhibitor is a peptide having a sequence at least 80% identical to a portion of SEQ ID NO:3.

Embodiment P15

The method of any one of embodiments P1 to P8, wherein the FOXM1 inhibitor is a peptide having a sequence at least 80% identical to a portion of mouse p19ARF protein.

Embodiment P16

The method of any one of embodiments P1 to P8, wherein the FOXM1 inhibitor is a peptide having a sequence at least 80% identical to a portion of SEQ ID NO:4.

Embodiment P17

The method of any one of embodiments P1 to P8, wherein the FOXM1 inhibitor is a peptide comprising the sequence KFVRSRRPRTASCALAFVN (SEQ ID NO:5).

Embodiment P18

The method of any one of embodiments P1 to P17, wherein the FOXM1 inhibitor reduces the interaction between FOXM1 and androgen receptor in the motor neuron.

Embodiment P19

The method of any one of embodiments P1 to P17, wherein the FOXM1 inhibitor reduces the interaction between FOXM1 and β-catenin in the motor neuron.

Embodiment P20

The method of any one of embodiments P1 to P17, wherein the FOXM1 inhibitor reduces the level of a FOXM1/androgen receptor/β-catenin complex in the motor neuron.

EXAMPLES

The following examples are for purposes of illustration and are not intended to limit the scope or spirit of the claims and disclosure.

One of the goals of the inventors was to screen for drugs that had cell specific antagonistic effects on AR. The inventors applied FRET-based AR conformation reporter assays in several cell lines to screen for a selective AR modulator. Jones et al, ACS Chem Biol, 3(7):412-8 (2008). The inventors discovered, inter alia, that thiazole antibiotics, and other FOXM1 inhibitors, had the ability to inhibit AR activity in a neuronal cell line but not a muscle cell line.

Thiostrepton has been shown to down-regulate the transcription factor FOXM1, which is a member of the forkhead box (FOX) protein family. FOX proteins have been reported to interact with hormone receptors. Madureira et al, J Biol Chem, 2006. 281(35): p. 25167-76; Lam et al, Nat Rev Cancer, 2013. 13(7): p. 482-95. Thiostrepton-induced AR inhibition may occur via FOXM1 regulation. In this disclosure, the inventors demonstrated that FOXM1 expression correlated with the ability of thiostrepton to inhibit AR activity in cells lines and that the mechanism of AR inhibition involved disruption of a FOXM1/β-catenin/AR transcriptional complex. Additionally, the inventors demonstrate herein that thiostrepton caused decreased expression of FOXM1 and selectively inhibited AR activity in motor neurons in vivo through the use of tissue-selective androgen-regulated genes. Otto-Duessel et al, Andrology, 1(1):29-36 (2013).

Activation of a polyglutamine tract-expanded androgen receptor (AR) is responsible for spinal and bulbar muscular atrophy, a neuromuscular disorder in which deterioration of motor neurons leads to progressive muscle weakness. While systemic AR inhibitors have been shown to ameliorate or prevent disease symptoms in mouse models, clinical trials with such agents in humans have had mixed results. Neuron-specific inhibition of AR activity may improve efficacy of treatments, as systemic inhibition of AR also impairs muscle function. The disclosure provides a screen for cell type-selective AR inhibitors, which resulted in the identification of a thiazole class of antibiotics that can inhibit AR activity in neuronal cell lines but not muscle cell lines. One of these antibiotics, thiostrepton, inhibits AR activity in neuronal GT1-7 cells with nanomolar potency. Treatment of rats with thiostrepton demonstrated AR antagonism in neurons, but not muscles. This selective inhibition is mediated in part by the inhibition of FOXM1 expression and activity, which causes altered subcellular localization of and altered association between AR and the AR co-activator beta-catenin. The results herein show that thiazole antibiotics, or other inhibitors of the AR-FOXM1 axis, can inhibit AR selectively in motor neurons, and will be useful in treating and preventing SBMA symptoms.

Experimental Materials and Methods. Cell lines: Most cells were obtained through the ATCC. GT1-7 cells were maintained in DMEM (Hyclone) media enriched with 10% fetal bovine serum (FBS), 1% sodium pyruvate (CellGro, Mediatech, VA) and 1% non-essential amino acids (Irvine Scientific, CA). 293, 3T3L, L6, and C2C12 cells (all obtained from the ATCC) were cultured in DMEM supplemented with 10% FBS. PC12 (ARQ112) cells, were cultured in DMEM supplemented with 10% FBS and 250 ng/mL deoxycyclin to induce AR expression. LNCaP C4 cells were grown in RPMI-1640 (CellGro) containing 10% FBS. TM4 cells were grown in a 1:1 mixture of Ham's F12 medium and Dulbecco's modified Eagle's medium with 1.2 g/L sodium bicarbonate and 15 mmol/L HEPES, 92.5%; horse serum, 5%; fetal bovine serum, 2.5%. ReNcell CX neural progenitor cells (Millipore) were grown on laminin coated plates in NSC maintenance media (Millipore) supplemented with EGF and FGF. All cultures were supplemented with 1% penicillin/streptomycin (Gibco, Life Technologies) and grown at 37° C. in humidified atmosphere containing 5% $CO_2$.

Creation of stable C-AR-Y reporter cell lines. Cell lines listed above were either transfected with a plasmid or a virus containing the CFP-AR-YFP construct preceding an IRES and hygromycin resistance gene and clonal stable cell lines selected. Qualification criteria for the transfected cell lines were described by Jones et al, ACS Chem Biol, 3(7):412-8 (2008).

Screen for AR-modulators. Screening was performed essentially as described by Jones et al, ACS Chem Biol, 3(7):412-8 (2008). Briefly, C-AR-Y reporter GTI-7 were transferred to 96 well plates and treated with library compounds for 24 hours. Each compound was tested on four different plates at a concentration of 1 umol/L. To half of the plates DHT (5 nmol/L) was added in order to identify AR antagonists. The compounds to be tested were from the NCI/DTP Open Chemical Repository's Approved Oncology Drugs Set II, Diversity Set II and Mechanistic Set. Control wells on each plate included non-transfected cells, no DHT (baseline signal), DHT (5 nmol/L) without library compound (maximal signal) plus DHT combined with hydroxyflutamide (1 umol/L) (AR antagonist). After 24 hours, medium was aspirated and FRET was measured as previously described using a monochromator-based fluorescence plate reader (M1000, Tecan, Inc.). Jones et al, ACS Chem Biol, 3(7):412-8 (2008). GT1-7 cells were used for primary screening and other cell lines mentioned above were used for secondary evaluation of candidate hits.

Luciferase Reporter Assay. Cells were transfected using Lipofectamine Plus (Invitrogen) with a normalization plasmid (pRL-SV40, Promega) and an androgen responsive plasmid (MMTV-luciferase or PSA-luciferase) as described in Jones et al, ACS Chem Biol, 3(7):412-8 (2008), and, where indicated, with an shRNA plasmid targeting FOXM1 (adapted for mouse FOXM1 sequence targeting) a scrambled control shRNA plasmid, or ARQ24 or ARQ65 plasmids. Christensen et al, PLoS One, 8(1):e54556 (2013). The following day, cells and drugs were distributed to 96-well plates. 24 hours later, luciferase activity was assessed by a dual luciferase assay kit (Promega) on the Tecan plate reader. Samples were run in quadruplicates and a Student's t test was performed to determine significance, where p<0.05 was considered significant.

Immunoprecipitation (IP). The co-IP assay was performed as described by Zhang et al, Cancer Cell, 20(4):427-42 (2011). In brief, cells were lysed on ice for 20 minutes in co-IP buffer containing 10 mmol/L Hepes (pH8), 300 mmol/L NaCL, 0.1 mmol/L EDTA, 20% glycerol, 0.2% NP-40 and protease inhibitor (Roche Diagnostics). Lysate was centrifuged at 10000 g for 10 minutes at 4° C. Lysate was incubated with primary antibody (β-catenin: rabbit, 9562, Cell Signaling Technology) overnight at 4° C. followed by incubation with 30 uL of Protein A/G beads for 2 hours at 4° C. Collected protein complexes were washed and analyzed by Western blotting.

Western Blot. Cell lysates was separated on a 6% SDS page gel and transferred to a nitrocellulose membrane. The membrane was blocked for one hour in 5% skim milk dissolved in TBS-T and probed with the following antibodies (1:10006): FoxM1 (rabbit, GeneTex), AR: 441 (mouse, Santa Cruz Biotechnology), β-catenin (rabbit 9562, Cell Signaling Technology), p84 (mouse, GeneTex) and actin (mouse, Santa Cruz Biotechnology). Horse radish peroxidase linked secondary antibodies were used along with ECL reagents for visualization. Western blots were quantified using Quantity One analysis software (BioRad).

Animals and Drugs. This study was carried out in strict accordance with the recommendations in the Guide for the Care and Use of Laboratory Animals of the National Institutes of Health. All experiments were performed under the IUCAC approval of City of Hope. Animals were purchased from Jackson Laboratory (Bar Harbor, Main). For the pilot pharmacokinetic experiment, nine male Sprague Dawley rats (n=3) were administered 1, 10, or 100 mg/kg intraperitoneal injections thrice per week for four weeks. One hour following the final dose, blood and spinal fluid were collected and analyzed by mass spectrometry. For the efficacy experiment, rats were divided into 3 groups (n=7) as follows: intact, castrated, and thiostrepton. Thiostrepton was dissolved in 20% DMSO and 80% PEG400 (Sigma Aldrich) and administered at a concentration of 50 mg/kg per day via an IP osmotic pump implant (Alzet). Following a treatment period of 7 days, rats were euthanized and organs harvested, weighed and processed for quantitative RT-PCR.

qRT-PCR. The quantitative RT-PCR method has been described by Jones et al, ACS Chem Biol, 3(7):412-8 (2008). In brief, dissected tissue was placed in RNA Later (Qiagen) before being homogenized using a bead homogenizer (TissueLyser, Qiagen). Following homogenization, RNA was isolated with an RNAEasy kit (Qiagen). RNA then was reverse transcribed (Promega, WI) and amplified (Qiagen Taq and reagents) on a StepOne PlusReal Time PCR System (Applied Biosystems), using SYBR green (Invitrogen) as the detecting dye and Rox (Invitrogen, CA) as the reference dye. Differences between experimental (x) and control (y) samples were normalized to RPL19 transcript levels (androgen unresponsive) and determined with the following calculation: $(2^{\wedge}(Ct_{sgene1}-Ct_{ygene1}))/(2^{\wedge}(Ct_{xRPL19}-Ct_{yRPL19}))$ One-way analysis of variance was applied to determine statistical significant among groups, where p<0.05 was considered significant.

Immunofluorescence. Cells were fixed in 2% paraformaldehyde prior to incubating with primary antibody (FOXM1: mouse, AbCam) overnight at 4° C. Following washing, secondary antibody (Alexa 954 goat anti-mouse, Invitrogen) was applied for 45 minutes at 37° C. After washing, slides were mounted and analyzed using a confocal microscope (Zeiss). The coloc-2 Image J plug-in (Fiji) was used to quantify co-localization of AR and FOXM1 from three independent samples using both Li's Intensity Correlation Quotient (ICQ) and Manders split coefficients co-localization values. One-way analysis of variance was applied to determine statistical significant among groups, where p<0.05 was considered significant.

Immunohistochemistry. Spinal cords were fixed in 10% neutral buffered formalin, embedded in paraffin and sectioned. Following de-waxing, slides were blocked with 10% normal goat serum for 30 minutes. The primary antibody (1:500) (AR: PG21, Millipore; FoxM1: GeneTex) was applied and incubated overnight at 4° C. Following three washes with TBS-T plus 0.1% Tween, slides were incubated with goat anti-rabbit antibody (1:200) for 30 minutes. Following three washes slides were incubated with Vectastain ABC reagent for 10 minutes at room temperature, then developed with DAB and counterstained with hematoxylin, dehydrated and mounted. A veterinary pathologist, blinded to the identity of the treatment groups, scored the spinal cord sections based on the intensity of FOXM1 expression, which was typically uniform across the entirety of a section, creating a scale ranging from 0-2 in both white matter and grey matter. Because few spinal cords were available for analysis, results from intact and castrated were grouped for analysis as 'untreated.' The staining between castrate and intact animals was very similar and distinct from thiostrepton treated animals. As a secondary quantification method, Image J was used to determine pixel density of FOXM1 staining. Images of 10 sections from 4 thiostrepton treated and 4 untreated rat slides were captured. Integrated density values were averaged (n=40) and a Student's t test was performed to determine significance, where p<0.05 was considered significant.

Figure 1B:
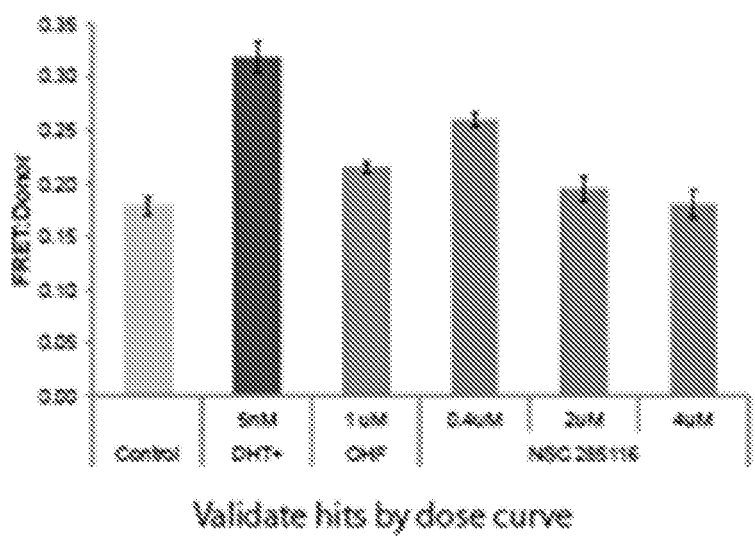

LC-MS/MS methods. Dried samples were resuspended in tetrahydrofuran spiked with 5 pg/µl reserpine, which was used as an instrument response control. Resuspended samples were separated with an Agilent 1290 UHPLC system (Agilent Technologies, Santa Clara, Calif.) and a Waters Acquity CSH $C_{18}$ column (Waters, Millford, Mass.) using a linear gradient from 95% buffer A (0.1% formic acid in 60% water/40% acetonitrile) to 100% buffer B (0.1% formic acid in 90% isopropanol/10% acetonitrile) over 2.5 minutes at 380 µL/minute. The UHPLC column eluent was sprayed into an Agilent 6490 triple quadrupole mass spectrometer equipped with a JetStream source (Agilent Technologies). Thiostrepton was detected by monitoring fragments from the doubly charged ion (m/z 832.9) at m/z 1247.4 and 1230.3. Data was analyzed using Agilent MassHunter quantitative analysis software.

dose response. FIG. 1B shows a dose dependent inhibition of DHT-induced AR conformation change by the compound NSC285116 (siomycin A) in GT1-7 cells. Once a dose response was observed, candidate compounds were then cross examined in CARY-expressing cell lines representing other tissues of interest, including muscle (C2C12), testes (TM4), kidney (HEK293), prostate (LNCaP C4), and adipose (3T3L1) (Table 1, where "AG" is agonist and "ANTAG" is antagonist). In addition to FRET, AR transcriptional activity was also assessed in several cell lines by transfecting cells with a luciferase reporter driven by the human PSA promoter. Bolton et al, Genes Dev, 21(16): 2005-17 (2007). After extensive testing in multiple cells lines (Table 2), siomycin A was identified as a neuron-selective AR inhibitor. Siomycin A showed greatest potency in neuronal GT1-7 cells, with some activity in HEK293 kidney cells, but little to no activity in LNCaP C4 prostate cancer, C2C12 muscle or 3T3L1 adipose-derived cells (Table 3).

Tables 1, 2, and 3 show that hits were assessed for agonist or antagonist activity in the indicated cell lines in a FRET or an androgen-responsive luciferase reporter assay. Siomycin A demonstrated antagonist activity in GT1-7 neuron cells but not C2C12 muscle cells and was therefore selected for further analysis.

TABLE 1

| | Luciferase | | | | | | | | | |
|---|---|---|---|---|---|---|---|---|---|---|
| | GT17 | | C2C12 | | HEK293 | | LNCaPC4 | | 3T3L1 | |
| Drug | AG | ANTAG | AG | ANTAG | AG | ANTAG | AG | ANTAG | AG | ANTAG |
| NSC3053 | | X | | X | | X | | | | X |
| NSC285116 Siomycin A | | X | | | | X | | | | |
| NSC631521 | X | | | | | | | | | |
| NSC631529 | | | | | | | | | | X |
| NSC690634 | | | X | | | | | X | | X |
| NSC71795 | X | | | | | | | X | | |
| NSC58514 | | | | | | | | X | | X |

Identification of GT1-7 specific AR inhibitors by high-throughput screening.

In order to identify potential cell-type selective AR modulators, the FRET-based assay of AR conformation change was utilized. AR signaling is a complex process involving many steps in addition to ligand binding. One crucial step is the ligand-induced conformational change of AR, which brings the carboxy (C)- and amino (N)-termini of the receptor together. Full length AR with cyan fluorescent protein (CFP) or yellow fluorescent protein (YFP) fused to either end (CARY) produces a FRET signal upon AR conformation change (FIG. 1A). This produces an accurate and quantifiable read-out of AR activity. Jones et al, ACS Chem Biol, 3(7):412-8 (2008). Because the interest was in the potential of neuron selective AR inhibitors for treatment of SBMA, the initial screen was carried out in CARY-transfected GT1-7 cells, which are a mouse model of hypothalamic neurons. Liposits et al, Endocrinology, 129(3): 1575-83 (1991). Cells were plated in 96 wells and treated with library compounds 24 hours prior to accessing conformational changes by FRET. Non-CARY cells, CARY cells without DHT (baseline signal), with DHT (5 nmol/L) only (maximal signal) and DHT combined with 1 µmol/L hydroxyflutamide (OHF) (AR antagonist) served as controls (FIG. 1A). Candidate hits were then further evaluated by

TABLE 2

| Cell Line | Lineage |
|---|---|
| GT1-7 | Murine hypothalamic tumor |
| HEK293 | Human kidney fibroblast |
| 3T3L1 | Murine adipocyte precursor |
| LNCaP C4 | Human prostate cancer |
| C2C12 | Murine myoblast |

TABLE 3

| | | | Luciferase | | |
|---|---|---|---|---|---|
| | | | C2C12 | | HEK293 |
| | GT1-7 | | An- | | An- |
| Drug | Agonist | Antagonist | Agonist | tagonist | Agonist | tagonist |
| NSC3053 | | X | | X | | X |
| NSC285116 Siomycin A | | X | | | | X |
| NSC631521 | X | | | | | |
| NSC631529 | X | | | | | |
| NSC690634 | X | | | | | |
| NSC71795 | X | | X | | X | |

TABLE 3-continued

| | Luciferase | | | | | |
|---|---|---|---|---|---|---|
| | GT1-7 | | C2C12 | | HEK293 | |
| Drug | Agonist | Antagonist | Agonist | Antagonist | Agonist | Antagonist |
| NSC641395 | X | | | | X | |
| NSC58514 | X | | | | | |

AR Inhibition by Thiazole Antibiotics

Figure 2A:
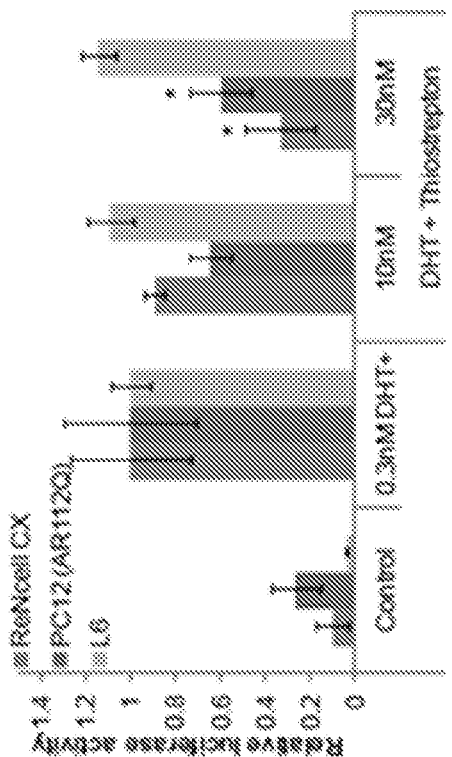
FIGS. 2A-2C show that thiazole antibiotics selectively inhibit AR in neuronal cells and have activity against polyQ-expanded AR.

Siomycin A is a thiazole class antibiotic that has been shown to inhibit transcriptional activity and expression of the FOXM1 transcription factor. Gartel, Cell Cycle, 11(18): 3341-2 (2012); Radhakrishnan et al, Cancer Res, 66(19): 9731-5 (2006); Gartel, Expert Opin Investig Drugs, 19(2): 235-42 (201). Thiostrepton belongs to the same class of antibiotics and has been reported to function similarly to siomycin. Hegde et al, Nat Chem, 3(9):725-31 (2011); Jiang et al, Int J Clin Exp Pathol, 7(9):5450-60 (2014); Kwok et al, Mol Cancer Ther, 7(7):2022-32 (2008). To test whether thiostrepton possessed similar AR antagonistic properties as siomycin, the ability of thiostrepton to inhibit AR transcriptional activity via luciferase assay in GT1-7 and C2C12 cells was assessed (FIG. 2A). Both thiostrepton and siomycin were found to selectively inhibit AR activity in GT1-7 cells, with thiostrepton having a greater potency.

As thiazole antibiotics have also been found to have effects on protesome function, we examined the activity of FDI-6, a selective FOXM1 inhibitor. Gormally et al, Nat Commun, 5:5165 (2014). The studies demonstrated that FDI-6 inhibited AR activity in GT1-7 cells but not C2C12 cells, demonstrating that anti-FOXM1 activity is the key to inhibit AR activity in these cells.

Figure 2B:
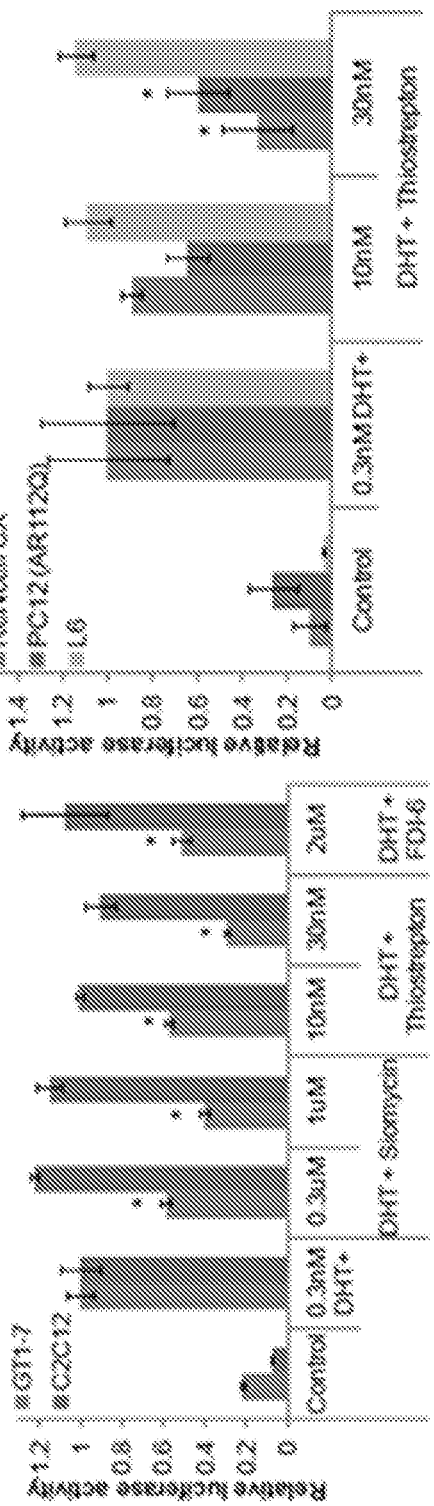

Further experimentation was conducted primarily with thiostrepton as it was the more potent of the FOXM1 inhibitors. The ability of thiostrepton to inhibit AR activity in additional neuronal cells, including ReNcell CX cells PC12 cells, and in rat L6 skeletal muscle cells was examined (FIG. 2B). Donato et al, BMC Neurosci, 8:36 (2007); Yaffe, Proc Natl Acad Sci USA, 61(2):477-83 (1968). The experiments demonstrated that thiostrepton inhibited AR activity in neuronal but not muscle cells, demonstrating that AR inhibition by FOXM1 inhibitors is neuron-selective.

Figure 2C:
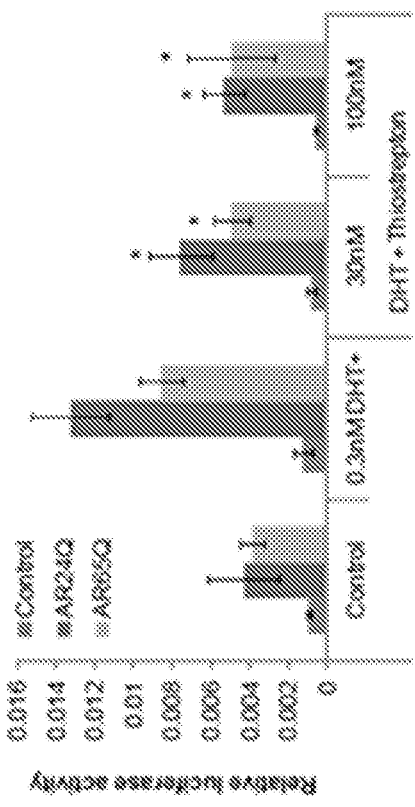

SBMA is caused by the activity of polyglutamine-expanded AR, and experiments were conducted to investigate the effects of thiostrepton against polyglutamine-expanded AR. AR-negative HEK293 cells were transfected with plasmids encoding AR with a 24 glutamine tract (normal) or with a 65 glutamine tract (disease associated). The polyglutamine-expanded AR was less transcriptionally active than the normal AR, as has been previously documented for such constructs. Kazemi-Esfarjani et al, Hum Mol Genet, 4:523-527 (1995). Thiostrepton inhibited the polyglutamine-expanded AR, as well as the non-expanded AR (FIG. 2C), demonstrating that thiostrepton inhibits the activity of a clinically relevant AR. In further support of this, the PC12 cells in FIG. 2B express an AR with a 112 glutamine tract, and thiostrepton efficiently inhibited AR activity in those cells as well.

FOXM1 Mediates AR Inhibition by Thiostrepton

FOX proteins can act as transcription factors and co-activators and have been shown to regulate AR transcriptional activity. Sahu et al, EMBO J, 30(19):3962-76 (2011); Yu et al, Ann NY Acad Sci, 1061:77-93 (2005). For instance, FOXA1 has been shown to interact and regulate transcription of both estrogen receptors and AR. Robinson, et al, Front Endocrinol (Lausanne), 3:68 (2012). Because thioazole antibiotics are known to inhibit FOXM1, the inventors speculated that thiostrepton-induced AR antagonistic effects might be mediated via FOXM1. To that end, FOXM1 expression levels were examined in different cell lines (FIG. 3A) and it was discovered that FOXM1 expression levels were highest in GT1-7, followed by 293HEK and LNCaP C4 cells. Little or no expression was observed in the remaining cell lines, demonstrating a correlation between FOXM1 expression and the inhibitory effect of thiostrepton on AR activity. Expression levels of the CARY construct did not correlate with sensitivity (FIG. 3A).

To further test the role of FOXM1 in association with AR activity, FOXM1 expression in GT1-7 cells was decreased using a lentiviral shRNA plasmid transfection. FOXM1 knock-down decreased the DHT-induced activity of AR, demonstrating that FOXM1 is an important AR coactivator in GT1-7 cells (FIG. 3B, Table 4). More importantly, decreasing FOXM1 expression diminished the potency of thiostrepton (compare DHT+thio/DHT alone ratio in control vs. FOXM1-silenced cells). This demonstrates that FOXM1 mediates the ability of thiostrepton to inhibit AR activity.

TABLE 4

| | | Fold Difference | P value |
|---|---|---|---|
| DHT-Vehicle | Control | 26.91 | 0.0002 |
| | FOXM1 shRNA | 12.81 | 0.0008 |
| DHT-10 nM thiostrepton | Control | 1.54 | 0.0040 |
| | FOXM1 shRNA | 1.34 | 0.0239 |
| DHT - 100 nM thiostrepton | Control | 2.04 | 0.0008 |
| | FOXM1 shRNA | 1.62 | 0.0057 |

It has been previously reported that thiostrepton causes decreased levels of FOXM1. Hegde et al, Nat Chem, 3(9): 725-31 (2011); Gartel, Front Oncol, 3:150 (2013). Treatment of GT1-7 CARY cells with thiostrepton resulted in slightly decreased FOXM1 levels compared to p84 loading control protein levels, both in the presence and absence of DHT (FIG. 3C), as shown from quantification of representative blots. In contrast to thiostrepton, DHT treatment increased FOXM1 levels, revealing the interplay between AR signaling pathway with FOXM1. AR levels themselves were not consistently decreased in response to thiostrepton treatment. FOXM1 has been shown to bind directly to β-catenin and facilitate its nuclear localization. The nuclear association between FOXM1 and β-catenin increases the transcriptional activity of both factors. Zhang et al, Cancer Cell, 20(4):427-42 (2011). β-catenin is a key AR coactivator in a variety of cells. Yang, J Biol Chem, 277(13):11336-44 (2002); Truica et al, Cancer Res, 60(17):4709-13 (2000). The inventors believed that thiostrepton could inhibit AR activity by limiting access to nuclear β-catenin via FOXM1 depletion. Nuclear and cytoplasmic fractions were isolated from GT1-7 cells treated with or without thiostrepton and DHT. Thiostrepton treatment caused lower levels of nuclear β-catenin, both phosphorylated and unphosphorylated (active) fractions (see doublet in FIG. 3D), demonstrating that thiostrepton treatment leads to β-catenin inactivation via its effects on FOXM1. As expected, control actin protein was observed primarily in cytoplasmic fraction.

Co-immunoprecipitation confirmed a direct interaction between β-catenin and FOXM1 as well as between β-catenin and AR (FIG. 3E). The amount of FOXM1 pulled down was reduced in thiostrepton-treated cells. While this may be due in part to the effects of thiostrepton on total FOXM1 levels, which is difficult to control for in these experiments, the decreased interaction between FOXM1 and β-catenin could have an effect on AR activity.

Figure 4A:
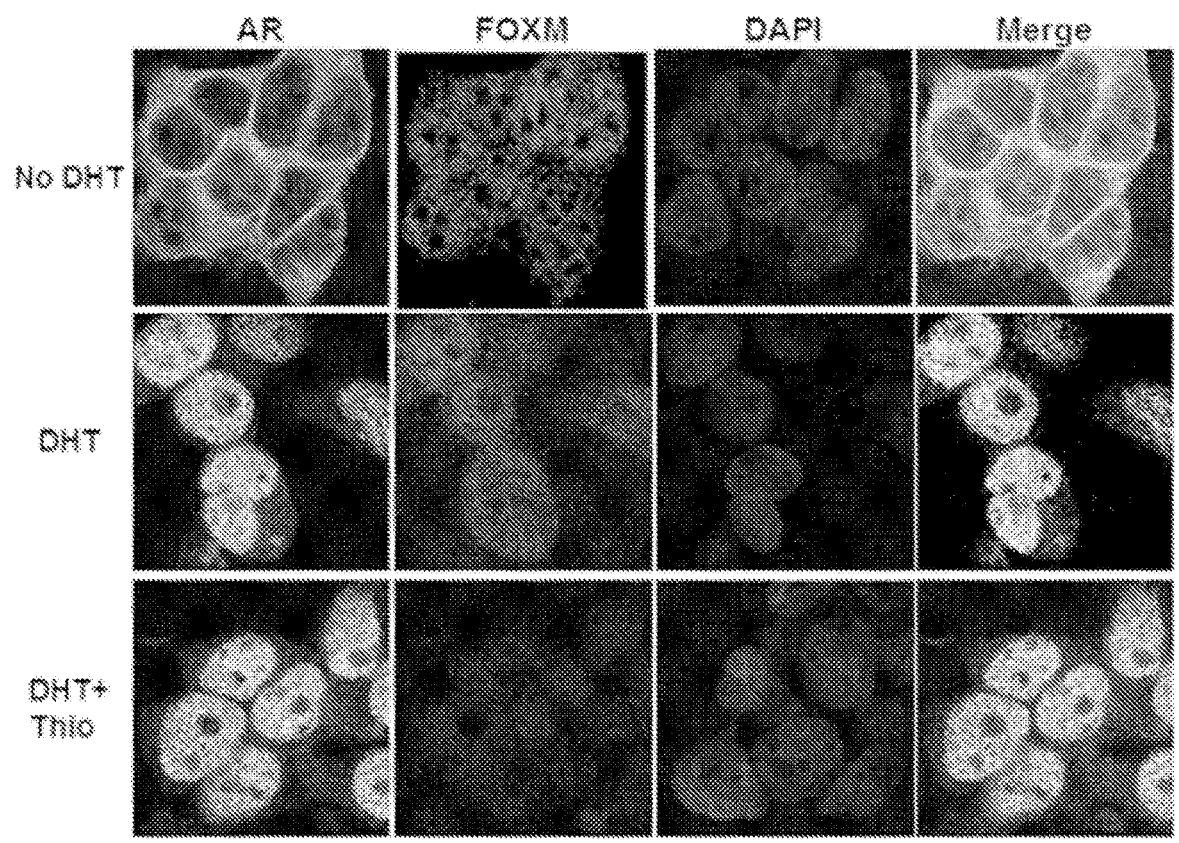
FIG. 4A shows GT1-7 cells expressing a YFP-tagged AR were treated as indicated for 24 hours prior to staining with anti-FOXM1 and DAPI.
Figure 4B:
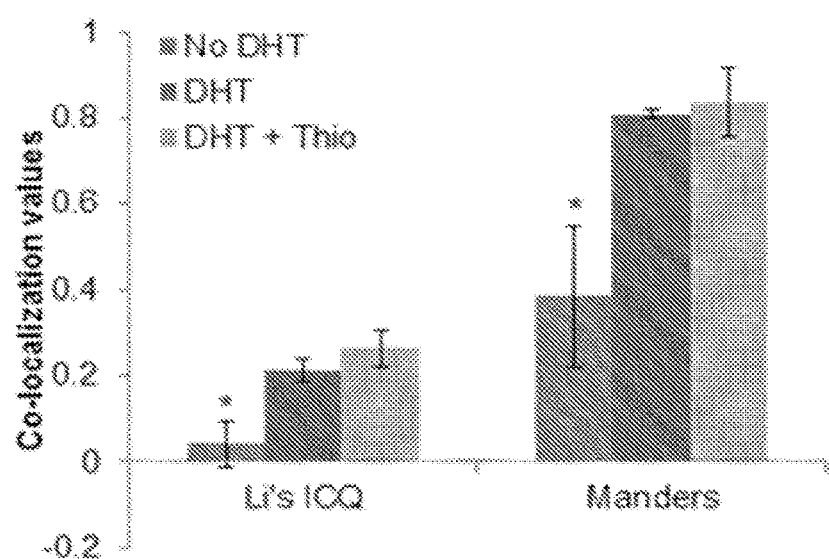
FIG. 4B shows the quantification and co-localization using image J demonstrates significant co-localization of FOXM1 and AR in the presence of DHT and DHT+thiostrepton by both Manders split coefficient and Li's ICQ value. Error bars represent the mean±SEM, $^aP<0.05$.

Using a co-IP assay in GT1-7 CARY cell lysates, no association was detected between AR and FOXM1 (data not shown). However, immunofluorescence staining demonstrated significant AR-FOXM1 co-localization in GT1-7 CARY cells (FIG. 4). Untreated cells predominantly expressed AR in the cytoplasm, while DHT treatment caused a shift to the nucleus. FOXM1 expression was mainly confined to the nucleus, which was true for untreated and treated cells. Image analysis revealed little to no co-localization between FOXM1 and AR in untreated cells (FIG. 4B). Addition of DHT increased association between FOXM1 and AR, which was not significantly affected by addition of thiostrepton. Although co-localization is not evidence of an interaction, these results show that FOXM1 and AR function together in the presence of DHT. In conclusion, this model demonstrates that thiostrepton decreases the levels of FOXM1, which leads to lower levels of nuclear β-catenin, an important AR coactivator, causing decreases transcriptional activity.

Thiostrepton treatment inhibits in vivo AR activity preferentially in rat spinal cord compared to skeletal muscle.

Figure 5A:
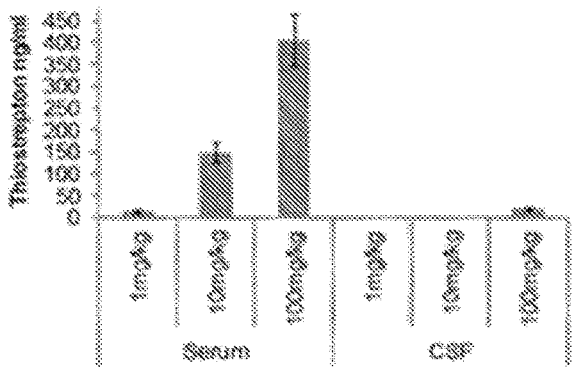
FIGS. 5A-5H show that thiostrepton treatment inhibits AR activity in rat spinal cord but not muscle.

A pilot pharmacokinetic study in rats was conducted to achieve desired dosing and to determine if thiostrepton crosses the blood brain barrier. Rats (n=3/group) received low (1 mg/kg), medium (10 mg/kg), or high (100 mg/kg) doses of thiostepton by intraperitoneal (IP) injection, three times a week for four weeks. One hour after the final dose, animals were euthanized and blood and spinal fluid was collected and analyzed by LC-MS/MS (FIG. 5A). A dose-dependent increase in plasma levels was discovered. Only the high dose of thiostrepton resulted in measurable levels of drug in the spinal fluid, showing that while the drug could cross the blood brain barrier, it existed in that compartment at much lower levels than the plasma. However, it did reach concentrations above its $IC_{50}$ as determined by luciferase assay in cultured cells, demonstrating that it would be active in motor neurons of the spinal cord.

Figure 5B:
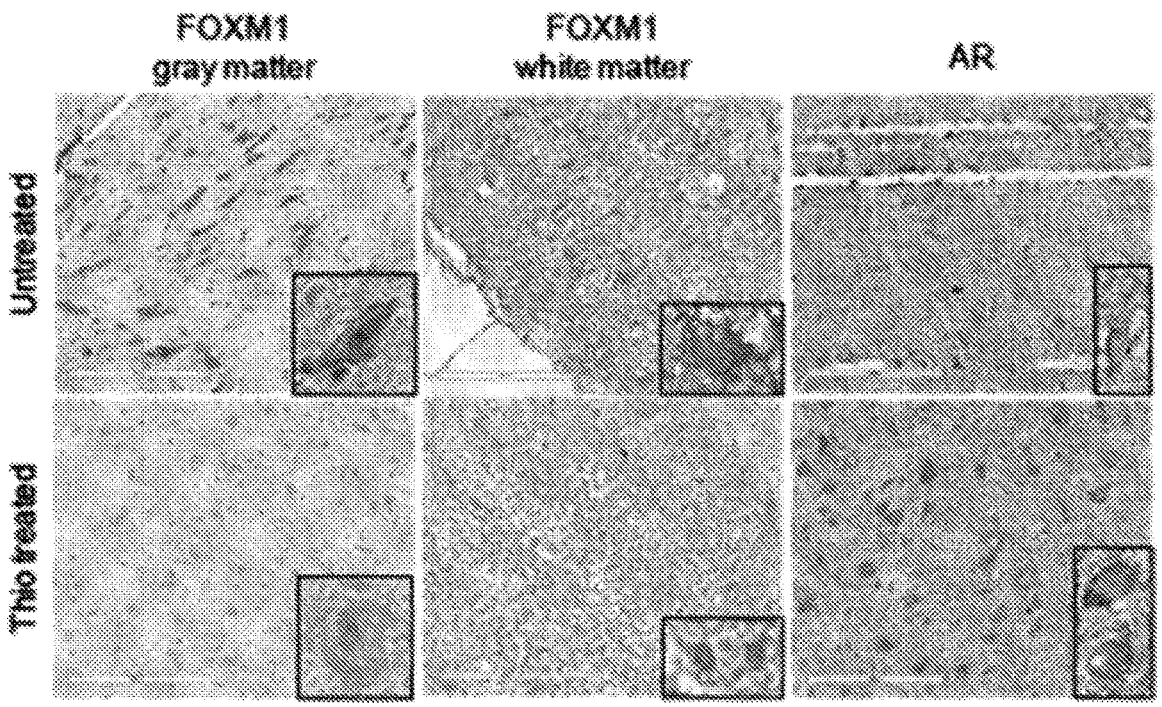
Figure 5C:
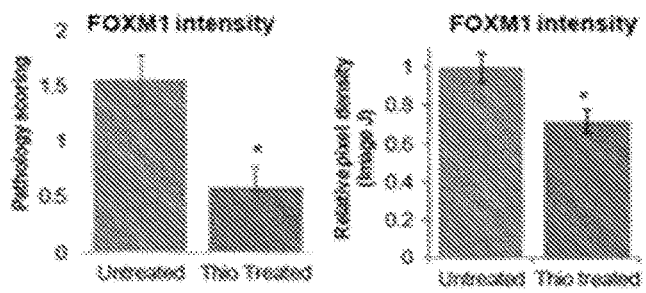
Figure 5D:
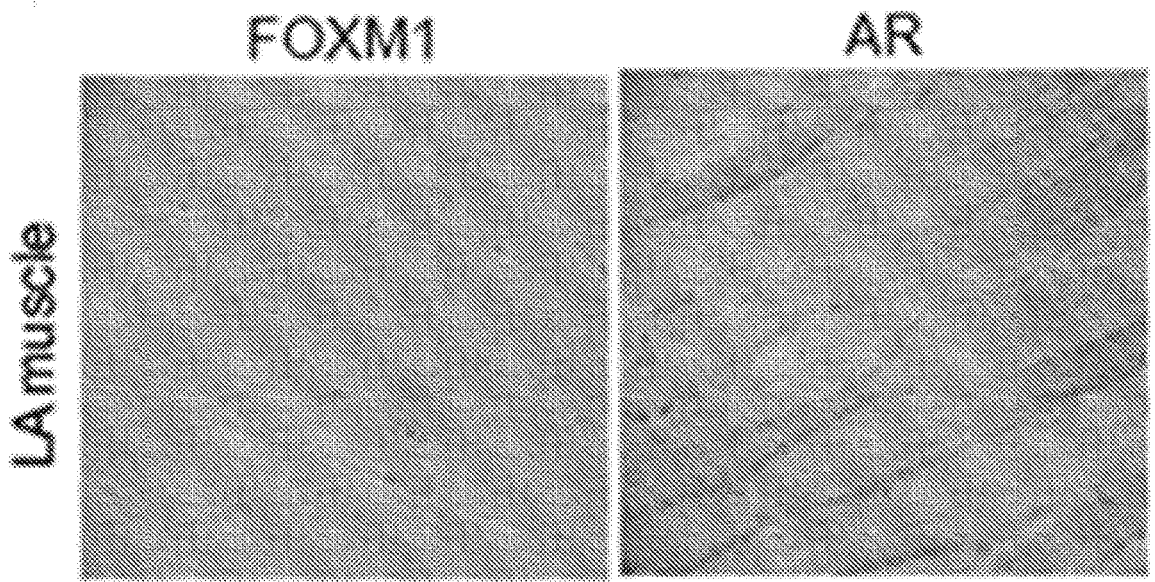
Figure 5E:
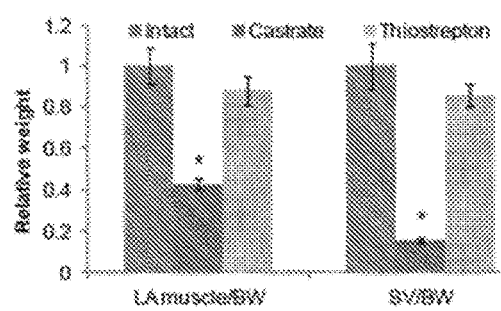

Based on these results, rats (n=7) were treated with 100 mg/kg per day thiostrepton or vehicle for four weeks using IP implanted osmotic pumps. Intact and castrate cohorts were included as controls. To test the efficacy of the thiostrepton in the motor neurons, the expression of FOXM1 in tissue sections of the spinal cord was examined. FOXM1 was located in both gray and white matter of the spinal cord (FIG. 5B), primarily in the nucleus, as had been shown by Zhang, J Mol Neurosci, 51(1):170-9 (2013). In the grey matter, FOXM1 was mainly found in the neurons. In the white matter, FOXM1 was found in glial cells, at least some of which appeared to be astrocytes; however, further immunohistochemistry would be necessary to confirm the identity of the cells. As scored by a veterinary pathologist blinded to treatment groups, treatment with thiostrepton significantly reduced the expression of FOXM1 in the spinal cord (FIG. 5C). As a secondary quantification method, Image J was used to determine pixel density of FOXM1 staining. Images of ten sections from four thiostrepton treated and four untreated slides were captured. Integrated density values were averaged and displayed relative to untreated control values (FIG. 5C). Thiostrepton treatment caused lower intensity FOXM1 staining (p=0.0036) by this method as well. This data demonstrated that functional levels of thiostrepton were present in the spinal cord and that it decreased FOXM1 levels in vivo, just as it did in cultured cells. AR was clearly observed in the nucleus and cytoplasm of neurons in both white and gray matter, and levels were not affected by thiostrepton, which parallels the cell culture data. Immunohistochemistry also revealed low to no expression of FOXM1 in intact muscle tissue (FIG. 5D), corroborating the cell culture data and in accordance with published literature where it has been reported that FOXM1 is highly expressed in embryonic muscle tissue, but is drastically reduced in adult skeletal muscle tissue. Bolte et al, PLoS One, 6(7):e22217 (2011). AR expression is evident in the striated muscle tissue nuclei as expected and is not affected by thiostrepton treatment.

Figure 5F:
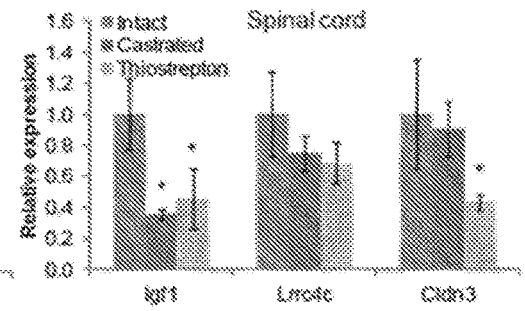
Figure 5G:
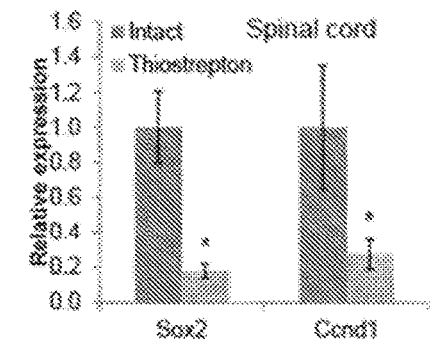
Figure 5H:
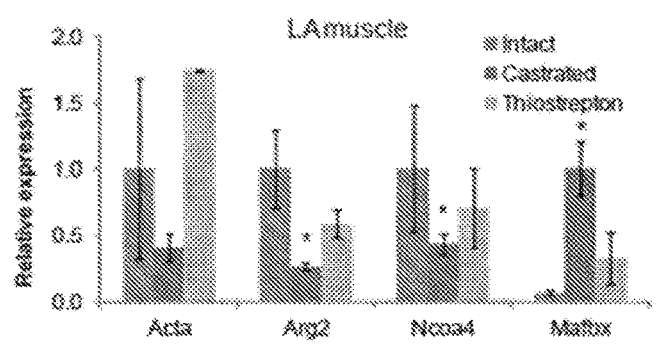

Androgens are known to control the growth and maintenance of the skeletal muscle and seminal vesicles. Hershberger et al, Proc Soc Exp Biol Med, 83(1):175-80 (1953). In order to investigate the impact of thiostrepton on these tissues, their weights at the end of the study were assessed. Compared to castrated rats, which displayed significantly reduced levator ani (LA) muscle (p<0.01) and seminal vesicles (SV) (p<0.01) weights, thiostrepton did not change LA and SV weights when compared to controls (FIG. 5B). This data demonstrates that thiostrepton does not significantly affect AR activity in muscle or SV, which is consistent with the cell culture findings. Because an equivalent androgen-dependent change in weight cannot be tested in motor neurons, the levels of tissue-selective androgen regulate genes, as a marker of AR activity, were assessed. These genes were identified in previous studies by the inventors. Otto-Duessel et al, Andrology, 1(1):29-36 (2013). RNA was isolated from spinal cord and LA muscle tissue and transcript levels were measured by RT-qPCR (FIG. 5F, FIG. 5H). Both castration and thiostrepton treatment caused decreases in three androgen-dependent genes, two of which were statistically significant with thiostrepton treatment, in the spinal cord compared to control treatment. In LA muscle, castration had a much greater effect than thiostrepton treatment at the four androgen-dependent genes analyzed, significantly altering the expression of 3 of 4 genes examined, while thiostrepton did not significantly affect the levels of any genes. Importantly, the transcript levels of FOXM1 target genes Ccndl and Sox2 were decreased in the spinal cords of thiostrepton-treated animals compared to intact controls, demonstrating on-target efficacy of the drug (FIG. 5G). Lee et al, PLoS One, 10:e0137703 (2015); Wang et al, Cancer Res, 67:8293-8300 (2007). This combined data demonstrates that thiostrepton inhibits AR activity in motor neurons but not LA muscle.

DISCUSSION

The inventors originally created the FRET-based AR conformation change reporter assay to identify novel AR inhibitors for use in prostate cancer. Jones et al, ACS Chem Biol, 3(7):412-8 (2008). The initial studied identified cell type selective AR inhibitors. The examples herein demonstrate the utility of the FRET-based AR conformation change reporter assay on a broader scale to identify cell type selective AR modulators with potential for clinical use in realms other than prostate cancer. The focus was to find a selective neuronal AR inhibitor with potential in treating SBMA. The data demonstrates that thiostrepton selectively inhibits AR in different cell lines in vitro. Based on literature demonstrating FOXM1 as a target of thiostrepton and other thiazole antibiotics, the inventors speculated that the decreased AR activity was mediated by decreased levels of FOXM1, a transcription factor involved in many different molecular pathways. Hegde et al, Nat Chem, 3(9):725-31

(2011); Gartel, Front Oncol, 3:150 (2013); Bhat et al, PLoS One, 4(5):e5592 (2009). The experiments herein demonstrate that FOXM1 is differentially expressed in a panel of cell lines and that this expression mostly correlates with the ability of thiazole antibiotics to inhibit AR activity. LNCaP C4 cells, which expressed FOXM1, were not as sensitive to siomycin in the initial screen. This could be due to the expression of a mutant AR in these cells; further investigation is warranted. Tan et al, Mol. Endocrinol., 11:450-459 (1997). The examples demonstrate that a chemically distinct FOXM1 inhibitor, FDI-6, inhibited AR activity in a neuronal but not muscle cells. Furthermore, manipulation of FOXM1 levels affected AR activity and sensitivity to thiostrepton, demonstrating that thiostrepton acts through FOXM1 to inhibit AR.

The experiments demonstrate that thiostrepton quantifiably reduced FOXM1 levels. Likewise, the experiments demonstrate that thiostrepton quantifiably reduced the nuclear levels of β-catenin in GT1-7 cells. Although only one blot was shown in each figure, each of the IP and Western blot experiments was repeated several times, with high reproducibility. While no interaction was detected between AR and FOXM1 by co-IP, confocal imaging demonstrated that these proteins function together in the nucleus in the presence of DHT. The co-IP experiments also demonstrated interactions between β-catenin and both AR and FOXM1. Zhang et al, Cancer Cell, 20(4):427-42 (2011); Yang et al, J Biol Chem, 277(13):11336-44 (2002). The data demonstrates that AR, FOXM1, and β-catenin form an active transcriptional complex in the nuclei of GT1-7 cells that is essential for full androgen-responsive transcription. Thiostrepton treatment reduced FOXM1 levels, which leads to lower levels of nuclear β-catenin, and thus reduced AR transcriptional activity.

Thiostrepton's selective inhibition of AR applies in vivo as well. Thiostrepton treatment did not inhibit AR activity in LA muscle or SV, as measured by changes in organ weights. It did cause decreased FOXM1 levels and inhibit androgen-regulated gene expression in spinal cord neurons. Although many of the RT-qPCR changes were not significant, this is likely due to the small number of animals in each group. The data herein demonstrates the successful identification of compounds that inhibit AR in spinal cord neurons but not muscle. Such drugs will be useful in the treatment of SBMA. In mouse models of SBMA, castration by physical or chemical means can prevent and/or ameliorate disease symptoms. Katsuno et al, Neuron, 35(5):843-54 (2002); Katsuno et al, Nat Med, 9(6):768-73 (2003). However, trials of androgen reducing agents in symptomatic humans have not had the same effect. Fischbeck et al, Ann Neurol, 65(2):119-20 (2009); Fernandez-Rhodes et al, Lancet Neurol, 10(2):140-7 (2011); Weydt et al, J Mol Neurosci, 2015. This could be in part because muscle atrophy has already occurred and androgens are needed to rebuild muscle tissue. Thus, a neuron selective AR inhibitor should inhibit degenerative AR activity while allowing the body's natural androgens to rebuild atrophied muscle tissue. As mentioned above, there is evidence that polyglutamine expanded AR has direct toxic effects in muscle cells, in which case a neuron-selective AR inhibitor would not benefit SBMA patients. Cortes et al, Neuron, 82(2):295-307 (2014). However, other studies show that knocking down neuronal AR while keeping muscle levels intact rescues the disease phenotype; genetic and RNA silencing approaches have not been able to settle the debate. Sahashi et al, Hum Mol Genet, 24:5985-5994 (2015). Testing thiostrepton or similar compounds in mouse models of SBMA could help answer this question. Sahashi et al, Hum Mol Genet, 2015; Katsuno et al, Cytogenet Genome Res, 100(1-4):243-51 (2003).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating spinal-bulbar muscular atrophy in a subject in need thereof, the method comprising administering to the subject a therapeutically effective amount of a compound selected from the group consisting of thiostrepton, Forkhead domain inhibitor-6 (FDI-6), a substituted FDI-6, a substituted thiostrepton, or a pharmaceutically acceptable salt of any one of the foregoing; wherein FDI-6 has the structure:

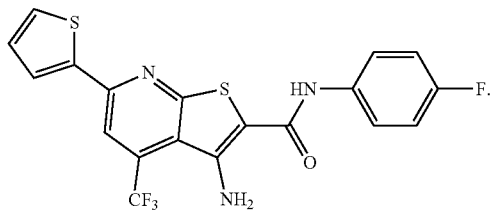 [SMILES: Nc1c(C(=O)Nc2ccc(F)cc2)sc2nc(-c3cccs3)cc(C(F)(F)F)c12]

2. The method of claim 1, wherein the compound is thiostrepton or a pharmaceutically acceptable salt thereof.

3. The method of claim 1, wherein the compound is FDI-6 or a pharmaceutically acceptable salt thereof.

4. A method of treating spinal-bulbar muscular atrophy in a subject in need thereof, the method comprising administering to the subject a therapeutically effective amount of a thiazole antibiotic.

* * * * *

SEQUENCE LISTING

```
<160> NUMBER OF SEQ ID NOS: 40

<210> SEQ ID NO 1
<211> LENGTH: 919
<212> TYPE: PRT
<213> ORGANISM: Homo sapiens

<400> SEQUENCE: 1

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Glu Thr
65                  70                  75                  80

Ser Pro Arg Gln Gln Gln Gln Gln Gly Glu Asp Gly Ser Pro Gln
                85                  90                  95

Ala His Arg Arg Gly Pro Thr Gly Tyr Leu Val Leu Asp Glu Glu Gln
            100                 105                 110
```

```
Gln Pro Ser Gln Pro Gln Ser Ala Leu Glu Cys His Pro Glu Arg Gly
        115                 120                 125

Cys Val Pro Glu Pro Gly Ala Val Ala Ala Ser Lys Gly Leu Pro
    130                 135                 140

Gln Gln Leu Pro Ala Pro Pro Asp Glu Asp Ser Ala Ala Pro Ser
145                 150                 155                 160

Thr Leu Ser Leu Leu Gly Pro Thr Phe Pro Gly Leu Ser Ser Cys Ser
                165                 170                 175

Ala Asp Leu Lys Asp Ile Leu Ser Glu Ala Ser Thr Met Gln Leu Leu
                180                 185                 190

Gln Gln Gln Gln Glu Ala Val Ser Glu Gly Ser Ser Ser Gly Arg
        195                 200                 205

Ala Arg Glu Ala Ser Gly Ala Pro Thr Ser Ser Lys Asp Asn Tyr Leu
    210                 215                 220

Gly Gly Thr Ser Thr Ile Ser Asp Asn Ala Lys Glu Leu Cys Lys Ala
225                 230                 235                 240

Val Ser Val Ser Met Gly Leu Gly Val Glu Ala Leu Glu His Leu Ser
                245                 250                 255

Pro Gly Glu Gln Leu Arg Gly Asp Cys Met Tyr Ala Pro Leu Leu Gly
        260                 265                 270

Val Pro Pro Ala Val Arg Pro Thr Pro Cys Ala Pro Leu Ala Glu Cys
    275                 280                 285

Lys Gly Ser Leu Leu Asp Asp Ser Ala Gly Lys Ser Thr Glu Asp Thr
290                 295                 300

Ala Glu Tyr Ser Pro Phe Lys Gly Gly Tyr Thr Lys Gly Leu Glu Gly
305                 310                 315                 320

Glu Ser Leu Gly Cys Ser Gly Ser Ala Ala Gly Ser Ser Gly Thr
        325                 330                 335

Leu Glu Leu Pro Ser Thr Leu Ser Leu Tyr Lys Ser Gly Ala Leu Asp
                340                 345                 350

Glu Ala Ala Ala Tyr Gln Ser Arg Asp Tyr Tyr Asn Phe Pro Leu Ala
        355                 360                 365

Leu Ala Gly Pro Pro Pro Pro Pro Pro His Pro His Ala Arg
    370                 375                 380

Ile Lys Leu Glu Asn Pro Leu Asp Tyr Gly Ser Ala Trp Ala Ala Ala
385                 390                 395                 400

Ala Ala Gln Cys Arg Tyr Gly Asp Leu Ala Ser Leu His Gly Ala Gly
            405                 410                 415

Ala Ala Gly Pro Gly Ser Gly Ser Pro Ser Ala Ala Ser Ser Ser
        420                 425                 430

Trp His Thr Leu Phe Thr Ala Glu Gly Gln Leu Tyr Gly Pro Cys
            435                 440                 445

Gly Gly Gly Gly Gly Gly Gly Gly Gly Gly Gly Gly Gly Gly
    450                 455                 460

Gly Gly Gly Gly Gly Gly Gly Glu Ala Gly Ala Val Ala Pro Tyr
465                 470                 475                 480

Gly Tyr Thr Arg Pro Pro Gln Gly Leu Ala Gly Gln Glu Ser Asp Phe
                485                 490                 495

Thr Ala Pro Asp Val Trp Tyr Pro Gly Gly Met Val Ser Arg Val Pro
            500                 505                 510

Tyr Pro Ser Pro Thr Cys Val Lys Ser Glu Met Gly Pro Trp Met Asp
            515                 520                 525
```

Ser Tyr Ser Gly Pro Tyr Gly Asp Met Arg Leu Glu Thr Ala Arg Asp
530                 535                 540

His Val Leu Pro Ile Asp Tyr Tyr Phe Pro Pro Gln Lys Thr Cys Leu
545                 550                 555                 560

Ile Cys Gly Asp Glu Ala Ser Gly Cys His Tyr Gly Ala Leu Thr Cys
            565                 570                 575

Gly Ser Cys Lys Val Phe Phe Lys Arg Ala Ala Glu Gly Lys Gln Lys
            580                 585                 590

Tyr Leu Cys Ala Ser Arg Asn Asp Cys Thr Ile Asp Lys Phe Arg Arg
        595                 600                 605

Lys Asn Cys Pro Ser Cys Arg Leu Arg Lys Cys Tyr Glu Ala Gly Met
    610                 615                 620

Thr Leu Gly Ala Arg Lys Leu Lys Lys Leu Gly Asn Leu Lys Leu Gln
625                 630                 635                 640

Glu Glu Gly Glu Ala Ser Ser Thr Thr Ser Pro Thr Glu Glu Thr Thr
                645                 650                 655

Gln Lys Leu Thr Val Ser His Ile Glu Gly Tyr Glu Cys Gln Pro Ile
            660                 665                 670

Phe Leu Asn Val Leu Glu Ala Ile Glu Pro Gly Val Val Cys Ala Gly
            675                 680                 685

His Asp Asn Asn Gln Pro Asp Ser Phe Ala Ala Leu Leu Ser Ser Leu
690                 695                 700

Asn Glu Leu Gly Glu Arg Gln Leu Val His Val Val Lys Trp Ala Lys
705                 710                 715                 720

Ala Leu Pro Gly Phe Arg Asn Leu His Val Asp Asp Gln Met Ala Val
                725                 730                 735

Ile Gln Tyr Ser Trp Met Gly Leu Met Val Phe Ala Met Gly Trp Arg
            740                 745                 750

Ser Phe Thr Asn Val Asn Ser Arg Met Leu Tyr Phe Ala Pro Asp Leu
        755                 760                 765

Val Phe Asn Glu Tyr Arg Met His Lys Ser Arg Met Tyr Ser Gln Cys
    770                 775                 780

Val Arg Met Arg His Leu Ser Gln Glu Phe Gly Trp Leu Gln Ile Thr
785                 790                 795                 800

Pro Gln Glu Phe Leu Cys Met Lys Ala Leu Leu Leu Phe Ser Ile Ile
                805                 810                 815

Pro Val Asp Gly Leu Lys Asn Gln Lys Phe Phe Asp Glu Leu Arg Met
            820                 825                 830

Asn Tyr Ile Lys Glu Leu Asp Arg Ile Ile Ala Cys Lys Arg Lys Asn
        835                 840                 845

Pro Thr Ser Cys Ser Arg Arg Phe Tyr Gln Leu Thr Lys Leu Leu Asp
    850                 855                 860

Ser Val Gln Pro Ile Ala Arg Glu Leu His Gln Phe Thr Phe Asp Leu
865                 870                 875                 880

Leu Ile Lys Ser His Met Val Ser Val Asp Phe Pro Glu Met Met Ala
                885                 890                 895

Glu Ile Ile Ser Val Gln Val Pro Lys Ile Leu Ser Gly Lys Val Lys
            900                 905                 910

Pro Ile Tyr Phe His Thr Gln
            915

<210> SEQ ID NO 2
<211> LENGTH: 801
<212> TYPE: PRT

<213> ORGANISM: Homo sapiens

<400> SEQUENCE: 2

Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
    130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
    210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
        275                 280                 285

Leu Ser Leu His Asp Met Phe Val Arg Glu Thr Ser Ala Asn Gly Lys
    290                 295                 300

Val Ser Phe Trp Thr Ile His Pro Ser Ala Asn Arg Tyr Leu Thr Leu
305                 310                 315                 320

Asp Gln Val Phe Lys Pro Leu Asp Pro Gly Ser Pro Gln Leu Pro Glu
                325                 330                 335

His Leu Glu Ser Gln Gln Lys Arg Pro Asn Pro Glu Leu Arg Arg Asn
            340                 345                 350

Met Thr Ile Lys Thr Glu Leu Pro Leu Gly Ala Arg Arg Lys Met Lys
        355                 360                 365

Pro Leu Leu Pro Arg Val Ser Ser Tyr Leu Val Pro Ile Gln Phe Pro
    370                 375                 380

Val Asn Gln Ser Leu Val Leu Gln Pro Ser Val Lys Val Pro Leu Pro
385                 390                 395                 400

-continued

```
Leu Ala Ala Ser Leu Met Ser Ser Glu Leu Ala Arg His Ser Lys Arg
                405                 410                 415
Val Arg Ile Ala Pro Lys Val Phe Gly Glu Gln Val Val Phe Gly Tyr
            420                 425                 430
Met Ser Lys Phe Phe Ser Gly Asp Leu Arg Asp Phe Gly Thr Pro Ile
        435                 440                 445
Thr Ser Leu Phe Asn Phe Ile Phe Leu Cys Leu Ser Val Leu Leu Ala
    450                 455                 460
Glu Glu Gly Ile Ala Pro Leu Ser Ser Ala Gly Pro Gly Lys Glu Glu
465                 470                 475                 480
Lys Leu Leu Phe Gly Glu Gly Phe Ser Pro Leu Pro Val Gln Thr
                485                 490                 495
Ile Lys Glu Glu Glu Ile Gln Pro Gly Glu Glu Met Pro His Leu Ala
            500                 505                 510
Arg Pro Ile Lys Val Glu Ser Pro Leu Glu Glu Trp Pro Ser Pro
        515                 520                 525
Ala Pro Ser Phe Lys Glu Glu Ser Ser His Ser Trp Glu Asp Ser Ser
    530                 535                 540
Gln Ser Pro Thr Pro Arg Pro Lys Lys Ser Tyr Ser Gly Leu Arg Ser
545                 550                 555                 560
Pro Thr Arg Cys Val Ser Glu Met Leu Val Ile Gln His Arg Glu Arg
                565                 570                 575
Arg Glu Arg Ser Arg Ser Arg Arg Lys Gln His Leu Leu Pro Pro Cys
            580                 585                 590
Val Asp Glu Pro Glu Leu Leu Phe Ser Glu Gly Pro Ser Thr Ser Arg
        595                 600                 605
Trp Ala Ala Glu Leu Pro Phe Pro Ala Asp Ser Ser Asp Pro Ala Ser
    610                 615                 620
Gln Leu Ser Tyr Ser Gln Glu Val Gly Gly Pro Phe Lys Thr Pro Ile
625                 630                 635                 640
Lys Glu Thr Leu Pro Ile Ser Ser Thr Pro Ser Lys Ser Val Leu Pro
                645                 650                 655
Arg Thr Pro Glu Ser Trp Arg Leu Thr Pro Pro Ala Lys Val Gly Gly
            660                 665                 670
Leu Asp Phe Ser Pro Val Gln Thr Ser Gln Gly Ala Ser Asp Pro Leu
        675                 680                 685
Pro Asp Pro Leu Gly Leu Met Asp Leu Ser Thr Thr Pro Leu Gln Ser
    690                 695                 700
Ala Pro Pro Leu Glu Ser Pro Gln Arg Leu Leu Ser Ser Glu Pro Leu
705                 710                 715                 720
Asp Leu Ile Ser Val Pro Phe Gly Asn Ser Ser Pro Ser Asp Ile Asp
                725                 730                 735
Val Pro Lys Pro Gly Ser Pro Glu Pro Gln Val Ser Gly Leu Ala Ala
            740                 745                 750
Asn Arg Ser Leu Thr Glu Gly Leu Val Leu Asp Thr Met Asn Asp Ser
        755                 760                 765
Leu Ser Lys Ile Leu Leu Asp Ile Ser Phe Pro Gly Leu Asp Glu Asp
    770                 775                 780
Pro Leu Gly Pro Asp Asn Ile Asn Trp Ser Gln Phe Ile Pro Glu Leu
785                 790                 795                 800
Gln
```

<210> SEQ ID NO 3

```
<211> LENGTH: 132
<212> TYPE: PRT
<213> ORGANISM: Homo sapiens

<400> SEQUENCE: 3

Met Val Arg Arg Phe Leu Val Thr Leu Arg Ile Arg Arg Ala Cys Gly
1               5                   10                  15

Pro Pro Arg Val Arg Val Phe Val Val His Ile Pro Arg Leu Thr Gly
                20                  25                  30

Glu Trp Ala Ala Pro Gly Ala Pro Ala Val Ala Leu Val Leu Met
        35                  40                  45

Leu Leu Arg Ser Gln Arg Leu Gly Gln Gln Pro Leu Pro Arg Arg Pro
    50                  55                  60

Gly His Asp Asp Gly Gln Arg Pro Ser Gly Ala Ala Ala Ala Pro
65                  70                  75                  80

Arg Arg Gly Ala Gln Leu Arg Arg Pro Arg His Ser His Pro Thr Arg
                85                  90                  95

Ala Arg Arg Cys Pro Gly Gly Leu Pro Gly His Ala Gly Gly Ala Ala
            100                 105                 110

Pro Gly Arg Gly Ala Ala Gly Arg Ala Arg Cys Leu Gly Pro Ser Ala
        115                 120                 125

Arg Gly Pro Gly
    130

<210> SEQ ID NO 4
<211> LENGTH: 169
<212> TYPE: PRT
<213> ORGANISM: Mus musculus

<400> SEQUENCE: 4

Met Gly Arg Arg Phe Leu Val Thr Val Arg Ile Gln Arg Ala Gly Arg
1               5                   10                  15

Pro Leu Gln Glu Arg Val Phe Leu Val Lys Phe Val Arg Ser Arg Arg
                20                  25                  30

Pro Arg Thr Ala Ser Cys Ala Leu Ala Phe Val Asn Met Leu Leu Arg
            35                  40                  45

Leu Glu Arg Ile Leu Arg Arg Gly Pro His Arg Asn Pro Gly Pro Gly
    50                  55                  60

Asp Asp Asp Gly Gln Arg Ser Arg Ser Ser Ser Ala Gln Leu Arg
65                  70                  75                  80

Cys Arg Phe Glu Leu Arg Gly Pro His Tyr Leu Leu Pro Pro Gly Ala
                85                  90                  95

Arg Arg Ser Ala Gly Arg Leu Pro Gly His Ala Gly Gly Ala Ala Arg
            100                 105                 110

Val Arg Gly Ser Ala Gly Cys Ala Arg Cys Leu Gly Ser Pro Ala Ala
        115                 120                 125

Arg Leu Gly Pro Arg Ala Gly Thr Ser Arg His Arg Ala Ile Phe Ala
    130                 135                 140

Phe Arg Trp Val Leu Phe Val Phe Arg Trp Val Val Phe Val Tyr Arg
145                 150                 155                 160

Trp Glu Arg Arg Pro Asp Arg Arg Ala
                165

<210> SEQ ID NO 5
<211> LENGTH: 19
<212> TYPE: PRT
<213> ORGANISM: Artificial sequence
```

<220> FEATURE:
<223> OTHER INFORMATION: synthetic polypeptide

<400> SEQUENCE: 5

Lys Phe Val Arg Ser Arg Arg Pro Arg Thr Ala Ser Cys Ala Leu Ala
1               5                   10                  15

Phe Val Asn

<210> SEQ ID NO 6
<211> LENGTH: 18
<212> TYPE: PRT
<213> ORGANISM: Artificial sequence
<220> FEATURE:
<223> OTHER INFORMATION: synthetic polypeptide

<400> SEQUENCE: 6

Lys Phe Val Arg Ser Arg Arg Pro Arg Thr Ala Ser Cys Ala Leu Ala
1               5                   10                  15

Phe Val

<210> SEQ ID NO 7
<211> LENGTH: 17
<212> TYPE: PRT
<213> ORGANISM: Artificial sequence
<220> FEATURE:
<223> OTHER INFORMATION: synthetic polypeptide

<400> SEQUENCE: 7

Lys Phe Val Arg Ser Arg Arg Pro Arg Thr Ala Ser Cys Ala Leu Ala
1               5                   10                  15

Phe

<210> SEQ ID NO 8
<211> LENGTH: 16
<212> TYPE: PRT
<213> ORGANISM: Artificial sequence
<220> FEATURE:
<223> OTHER INFORMATION: synthetic polypeptide

<400> SEQUENCE: 8

Lys Phe Val Arg Ser Arg Arg Pro Arg Thr Ala Ser Cys Ala Leu Ala
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: synthetic polypeptide

<400> SEQUENCE: 9

Lys Phe Val Arg Ser Arg Arg Pro Arg Thr Ala Ser Cys Ala Leu
1               5                   10                  15

<210> SEQ ID NO 10
<211> LENGTH: 14
<212> TYPE: PRT
<213> ORGANISM: Artificial sequence
<220> FEATURE:
<223> OTHER INFORMATION: synthetic polypeptide

<400> SEQUENCE: 10

Lys Phe Val Arg Ser Arg Arg Pro Arg Thr Ala Ser Cys Ala
1               5                   10

<210> SEQ ID NO 11
<211> LENGTH: 13
<212> TYPE: PRT
<213> ORGANISM: Artificial sequence
<220> FEATURE:
<223> OTHER INFORMATION: synthetic polypeptide

<400> SEQUENCE: 11

Lys Phe Val Arg Ser Arg Arg Pro Arg Thr Ala Ser Cys
1               5                   10

<210> SEQ ID NO 12
<211> LENGTH: 12
<212> TYPE: PRT
<213> ORGANISM: Artificial sequence
<220> FEATURE:
<223> OTHER INFORMATION: synthetic polypeptide

<400> SEQUENCE: 12

Lys Phe Val Arg Ser Arg Arg Pro Arg Thr Ala Ser
1               5                   10

<210> SEQ ID NO 13
<211> LENGTH: 11
<212> TYPE: PRT
<213> ORGANISM: Artificial sequence
<220> FEATURE:
<223> OTHER INFORMATION: synthetic polypeptide

<400> SEQUENCE: 13

Lys Phe Val Arg Ser Arg Arg Pro Arg Thr Ala
1               5                   10

<210> SEQ ID NO 14
<211> LENGTH: 10
<212> TYPE: PRT
<213> ORGANISM: Artificial sequence
<220> FEATURE:
<223> OTHER INFORMATION: synthetic polypeptide

<400> SEQUENCE: 14

Lys Phe Val Arg Ser Arg Arg Pro Arg Thr
1               5                   10

<210> SEQ ID NO 15
<211> LENGTH: 9
<212> TYPE: PRT
<213> ORGANISM: Artificial sequence
<220> FEATURE:
<223> OTHER INFORMATION: synthetic polypeptide

<400> SEQUENCE: 15

Lys Phe Val Arg Ser Arg Arg Pro Arg
1               5

<210> SEQ ID NO 16
<211> LENGTH: 8
<212> TYPE: PRT
<213> ORGANISM: Artificial sequence
<220> FEATURE:
<223> OTHER INFORMATION: synthetic polypeptide

<400> SEQUENCE: 16

Lys Phe Val Arg Ser Arg Arg Pro
1               5

```
<210> SEQ ID NO 17
<211> LENGTH: 7
<212> TYPE: PRT
<213> ORGANISM: Artificial sequence
<220> FEATURE:
<223> OTHER INFORMATION: synthetic polypeptide

<400> SEQUENCE: 17

Lys Phe Val Arg Ser Arg Arg
1               5

<210> SEQ ID NO 18
<211> LENGTH: 6
<212> TYPE: PRT
<213> ORGANISM: Artificial sequence
<220> FEATURE:
<223> OTHER INFORMATION: synthetic polypeptide

<400> SEQUENCE: 18

Lys Phe Val Arg Ser Arg
1               5

<210> SEQ ID NO 19
<211> LENGTH: 5
<212> TYPE: PRT
<213> ORGANISM: Artificial sequence
<220> FEATURE:
<223> OTHER INFORMATION: synthetic polypeptide

<400> SEQUENCE: 19

Lys Phe Val Arg Ser
1               5

<210> SEQ ID NO 20
<211> LENGTH: 18
<212> TYPE: PRT
<213> ORGANISM: Artificial sequence
<220> FEATURE:
<223> OTHER INFORMATION: synthetic polypeptide

<400> SEQUENCE: 20

Phe Val Arg Ser Arg Arg Pro Arg Thr Ala Ser Cys Ala Leu Ala Phe
1               5                   10                  15

Val Asn

<210> SEQ ID NO 21
<211> LENGTH: 17
<212> TYPE: PRT
<213> ORGANISM: Artificial sequence
<220> FEATURE:
<223> OTHER INFORMATION: synthetic polypeptide

<400> SEQUENCE: 21

Val Arg Ser Arg Arg Pro Arg Thr Ala Ser Cys Ala Leu Ala Phe Val
1               5                   10                  15

Asn

<210> SEQ ID NO 22
<211> LENGTH: 16
<212> TYPE: PRT
<213> ORGANISM: Artificial sequence
<220> FEATURE:
<223> OTHER INFORMATION: synthetic polypeptide

<400> SEQUENCE: 22

Arg Ser Arg Arg Pro Arg Thr Ala Ser Cys Ala Leu Ala Phe Val Asn
```

<210> SEQ ID NO 23
<211> LENGTH: 15
<212> TYPE: PRT
<213> ORGANISM: Artificial sequence
<220> FEATURE:
<223> OTHER INFORMATION: synthetic polypeptide

<400> SEQUENCE: 23

Ser Arg Arg Pro Arg Thr Ala Ser Cys Ala Leu Ala Phe Val Asn
1               5                   10                  15

<210> SEQ ID NO 24
<211> LENGTH: 14
<212> TYPE: PRT
<213> ORGANISM: Artificial sequence
<220> FEATURE:
<223> OTHER INFORMATION: synthetic polypeptide

<400> SEQUENCE: 24

Arg Arg Pro Arg Thr Ala Ser Cys Ala Leu Ala Phe Val Asn
1               5                   10

<210> SEQ ID NO 25
<211> LENGTH: 13
<212> TYPE: PRT
<213> ORGANISM: Artificial sequence
<220> FEATURE:
<223> OTHER INFORMATION: synthetic polypeptide

<400> SEQUENCE: 25

Arg Pro Arg Thr Ala Ser Cys Ala Leu Ala Phe Val Asn
1               5                   10

<210> SEQ ID NO 26
<211> LENGTH: 12
<212> TYPE: PRT
<213> ORGANISM: Artificial sequence
<220> FEATURE:
<223> OTHER INFORMATION: synthetic polypeptide

<400> SEQUENCE: 26

Pro Arg Thr Ala Ser Cys Ala Leu Ala Phe Val Asn
1               5                   10

<210> SEQ ID NO 27
<211> LENGTH: 11
<212> TYPE: PRT
<213> ORGANISM: Artificial sequence
<220> FEATURE:
<223> OTHER INFORMATION: synthetic polypeptide

<400> SEQUENCE: 27

Arg Thr Ala Ser Cys Ala Leu Ala Phe Val Asn
1               5                   10

<210> SEQ ID NO 28
<211> LENGTH: 10
<212> TYPE: PRT
<213> ORGANISM: Artificial sequence
<220> FEATURE:
<223> OTHER INFORMATION: synthetic polypeptide

<400> SEQUENCE: 28

Thr Ala Ser Cys Ala Leu Ala Phe Val Asn
1               5                   10

<210> SEQ ID NO 29
<211> LENGTH: 9
<212> TYPE: PRT
<213> ORGANISM: Artificial sequence
<220> FEATURE:
<223> OTHER INFORMATION: synthetic polypeptide

<400> SEQUENCE: 29

Ala Ser Cys Ala Leu Ala Phe Val Asn
1               5

<210> SEQ ID NO 30
<211> LENGTH: 8
<212> TYPE: PRT
<213> ORGANISM: Artificial sequence
<220> FEATURE:
<223> OTHER INFORMATION: synthetic polypeptide

<400> SEQUENCE: 30

Ser Cys Ala Leu Ala Phe Val Asn
1               5

<210> SEQ ID NO 31
<211> LENGTH: 7
<212> TYPE: PRT
<213> ORGANISM: Artificial sequence
<220> FEATURE:
<223> OTHER INFORMATION: synthetic polypeptide

<400> SEQUENCE: 31

Cys Ala Leu Ala Phe Val Asn
1               5

<210> SEQ ID NO 32
<211> LENGTH: 6
<212> TYPE: PRT
<213> ORGANISM: Artificial sequence
<220> FEATURE:
<223> OTHER INFORMATION: synthetic polypeptide

<400> SEQUENCE: 32

Ala Leu Ala Phe Val Asn
1               5

<210> SEQ ID NO 33
<211> LENGTH: 5
<212> TYPE: PRT
<213> ORGANISM: Artificial sequence
<220> FEATURE:
<223> OTHER INFORMATION: synthetic polypeptide

<400> SEQUENCE: 33

Leu Ala Phe Val Asn
1               5

<210> SEQ ID NO 34
<211> LENGTH: 17
<212> TYPE: PRT
<213> ORGANISM: Artificial sequence
<220> FEATURE:
<223> OTHER INFORMATION: synthetic polypeptide

<400> SEQUENCE: 34

Phe Val Arg Ser Arg Arg Pro Arg Thr Ala Ser Cys Ala Leu Ala Phe
1               5                   10                  15

Val

<210> SEQ ID NO 35
<211> LENGTH: 15
<212> TYPE: PRT
<213> ORGANISM: Artificial sequence
<220> FEATURE:
<223> OTHER INFORMATION: synthetic polypeptide

<400> SEQUENCE: 35

Val Arg Ser Arg Arg Pro Arg Thr Ala Ser Cys Ala Leu Ala Phe
1               5                   10                  15

<210> SEQ ID NO 36
<211> LENGTH: 13
<212> TYPE: PRT
<213> ORGANISM: Artificial sequence
<220> FEATURE:
<223> OTHER INFORMATION: synthetic polypeptide

<400> SEQUENCE: 36

Arg Ser Arg Arg Pro Arg Thr Ala Ser Cys Ala Leu Ala
1               5                   10

<210> SEQ ID NO 37
<211> LENGTH: 11
<212> TYPE: PRT
<213> ORGANISM: Artificial sequence
<220> FEATURE:
<223> OTHER INFORMATION: synthetic polypeptide

<400> SEQUENCE: 37

Ser Arg Arg Pro Arg Thr Ala Ser Cys Ala Leu
1               5                   10

<210> SEQ ID NO 38
<211> LENGTH: 9
<212> TYPE: PRT
<213> ORGANISM: Artificial sequence
<220> FEATURE:
<223> OTHER INFORMATION: synthetic polypeptide

<400> SEQUENCE: 38

Arg Arg Pro Arg Thr Ala Ser Cys Ala
1               5

<210> SEQ ID NO 39
<211> LENGTH: 7
<212> TYPE: PRT
<213> ORGANISM: Artificial sequence
<220> FEATURE:
<223> OTHER INFORMATION: synthetic polypeptide

<400> SEQUENCE: 39

Arg Pro Arg Thr Ala Ser Cys
1               5

```
<210> SEQ ID NO 40
<211> LENGTH: 6
<212> TYPE: PRT
<213> ORGANISM: Artificial sequence
<220> FEATURE:
<223> OTHER INFORMATION: synthetic polypeptide

<400> SEQUENCE: 40

Lys Pro Arg Thr Ala Ser
1               5
```